United States Patent
Wang et al.

(10) Patent No.: US 9,493,812 B2
(45) Date of Patent: Nov. 15, 2016

(54) METHOD FOR DETECTING A TARGET ANALYTE THAT EXHIBITS PROTEASE ENZYME ACTIVITY

(71) Applicant: Abbott Point of Care Inc., Princeton, NJ (US)

(72) Inventors: Dan Wang, Kanata (CA); G. Bruce Collier, Fitzroy Harbour (CA)

(73) Assignee: Abbott Point of Care, Princeton, NJ (US)

( * ) Notice: Subject to any disclaimer, the term of this patent is extended or adjusted under 35 U.S.C. 154(b) by 0 days.

(21) Appl. No.: 14/974,244

(22) Filed: Dec. 18, 2015

(65) Prior Publication Data

US 2016/0102337 A1  Apr. 14, 2016

Related U.S. Application Data

(62) Division of application No. 14/206,776, filed on Mar. 12, 2014, now Pat. No. 9,249,450.

(60) Provisional application No. 61/787,343, filed on Mar. 15, 2013.

(51) Int. Cl.
   *C12Q 1/37* (2006.01)
   *G01N 27/327* (2006.01)
   (Continued)

(52) U.S. Cl.
   CPC ............... *C12Q 1/37* (2013.01); *B01L 3/502* (2013.01); *C12N 9/0004* (2013.01); *G01N 27/3271* (2013.01); *G01N 27/3273* (2013.01); *B01L 2200/04* (2013.01); *B01L 2200/0684* (2013.01); *B01L 2300/0645* (2013.01);
   (Continued)

(58) Field of Classification Search
   None
   See application file for complete search history.

(56) References Cited

U.S. PATENT DOCUMENTS

| | | |
|---|---|---|
| 4,954,087 A | 9/1990 | Lauks et al. |
| 5,200,051 A | 4/1993 | Cozzette et al. |
| 5,514,253 A | 5/1996 | Davis et al. |

(Continued)

FOREIGN PATENT DOCUMENTS

| | | |
|---|---|---|
| EP | 1277839 | 1/2003 |
| WO | 9910736 | 3/1999 |
| WO | 2014150883 | 9/2014 |

OTHER PUBLICATIONS

Chica et al. Curr Opin Biotechnol. Aug. 2005;16(4):378-84.*
(Continued)

*Primary Examiner* — Christian Fronda
(74) *Attorney, Agent, or Firm* — Kilpatrick Townsend & Stockton LLP

(57) ABSTRACT

The described invention provides a method for detecting a target analyte that exhibits protease enzyme activity. The described method includes contacting a sample with a hybrid oxidase enzyme engineered to exhibit increased catalytic activity over that of a starting oxidase enzyme upon cleavage of a mutated protease cleavage recognition sequence. The mutated protease cleavage recognition sequence is a recognition sequence specific for the target analyte. The described method further includes contacting a substrate with the engineered hybrid oxidase enzyme. The substrate comprises a cognate composition of matter to the engineered hybrid oxidase enzyme, and the engineered hybrid oxidase enzyme is configured to catalyze conversion of the cognate composition of matter into a detectable product upon proteolytic cleavage of the mutated protease cleavage recognition sequence by the target analyte.

5 Claims, 9 Drawing Sheets

(51) Int. Cl.
*B01L 3/00* (2006.01)
*C12N 9/02* (2006.01)
(52) U.S. Cl.
CPC .......... *B01L 2400/0487* (2013.01); *B01L 2400/0694* (2013.01); *G01N 2333/95* (2013.01)

(56) References Cited

U.S. PATENT DOCUMENTS

| | | | |
|---|---|---|---|
| 5,554,339 | A | 9/1996 | Cozzette et al. |
| 5,821,399 | A | 10/1998 | Zelin |
| 6,030,827 | A | 2/2000 | Davis et al. |
| 7,682,833 | B2 | 3/2010 | Miller et al. |
| 7,723,099 | B2 | 5/2010 | Miller et al. |
| 2004/0091989 | A1 | 5/2004 | Inagaki et al. |
| 2006/0228790 | A1 | 10/2006 | Inagaki et al. |
| 2013/0343955 | A1 | 12/2013 | Doyle et al. |
| 2014/0295476 | A1 | 10/2014 | Wang et al. |

OTHER PUBLICATIONS

Sen et al. Appl Biochem Biotechnol. Dec. 2007;143(3):212-23.*
U.S. Appl. No. 14/206,776, Non-Final Office Action mailed on May 7, 2015, 8 pages.
U.S. Appl. No. 14/206,776, Notice of Allowance mailed on Sep. 24, 2015, 5 pages.
U.S. Appl. No. 14/206,776, Restriction Requirement mailed on Feb. 20, 2015, 6 pages.
Arima et al., Recombinant expression, biochemical characterization and stabilization through proteolysis of an L-glutamate oxidase from Streptomyces sp. X-119-6, Journal of Biochemistry, vol. 134, No. 6, Dec. 1, 2003, pp. 805-812.
Chang, Thrombin specificity. Requirement for apolar amino acids adjacent to the thrombin cleavage site of polypeptide substrate, European Journal of Biochemistry, vol. 151, No. 2, Sep. 2, 1985, pp. 217-224.
Chen et al., A common precursor for the three subunits of L-glutamate oxidase encoded by gox gene from Streptomyces platensis NTU3304, Canadian Journal of Microbiology, vol. 47, No. 3, Mar. 2001, pp. 269-275.
Chica et al., Semi-rational approaches to engineering enzyme activity: combining the benefits of directed evolution and rational design, Current Opinion in Biotechnology, vol. 16, No. 4, Aug. 2005, pp. 378-384.
Ionescu et al., Protease amperometric sensor, Analytical Chemistry, vol. 78, No. 18, Sep. 15, 2006, pp. 6327-6331.
International Application No. PCT/US2014/024453, International Preliminary Report on Patentability mailed on Sep. 15, 2015, 6 pages.
International Application No. PCT/US2014/024453, International Search Report and Written Opinion mailed on Jul. 16, 2014, 10 pages.
Sen et al., Developments in directed evolution for improving enzyme functions, Applied Biochemistry and Biotechnology, vol. 143, No. 3, Dec. 2007, pp. 212-223.
Shin et al., Micropatterned surfaces functionalized with electroactive peptides for detecting protease release from cells, Analytical Chemistry, vol. 85, No. 1, Jan. 2, 2013, pp. 220-227.
Wu et al., A novel electrochemical biosensor for highly selective detection of protease biomarker from Bacillus licheniformis with D-amino acid containing peptide, Analyst, vol. 137, No. 20, Oct. 21, 2012, pp. 4829-4833.

* cited by examiner

First Contacting Step

Second Contacting Step

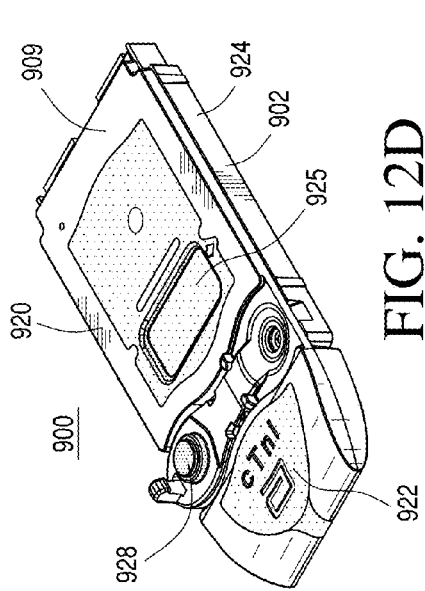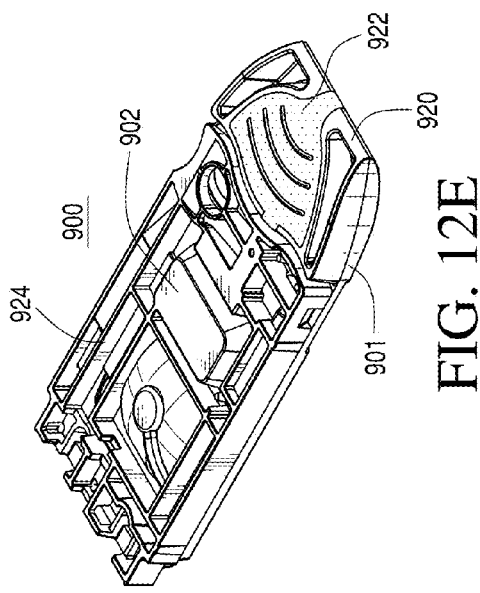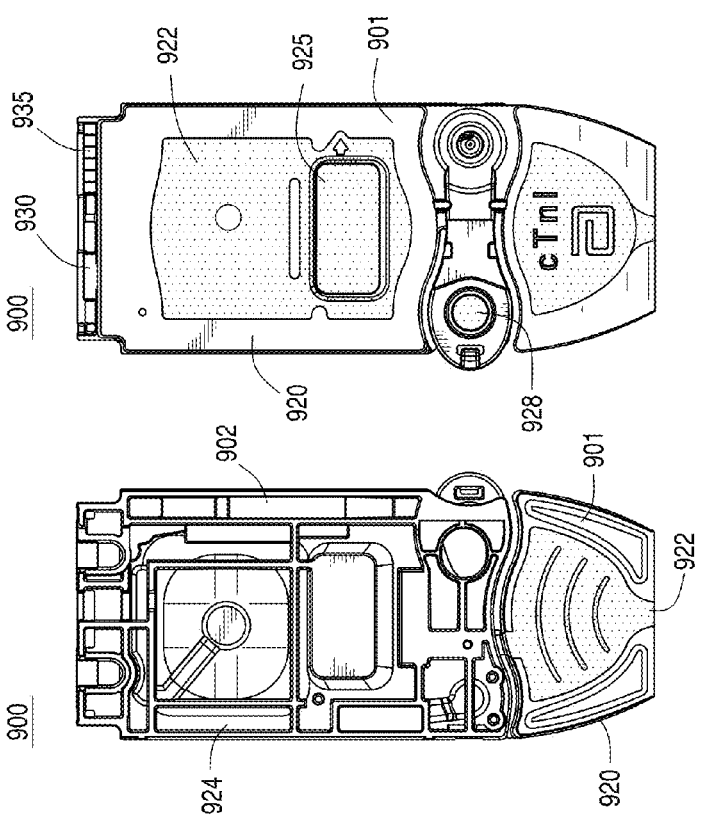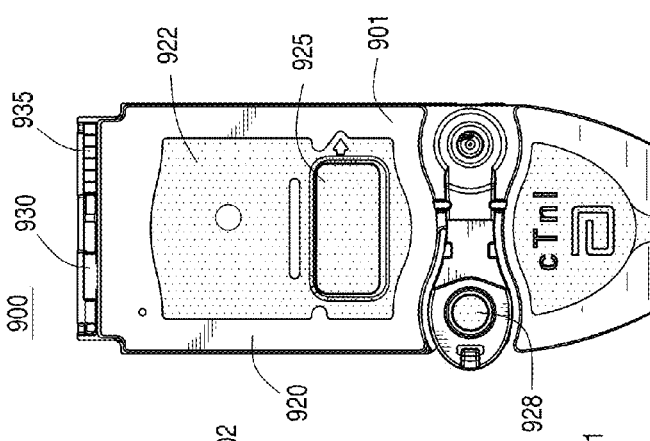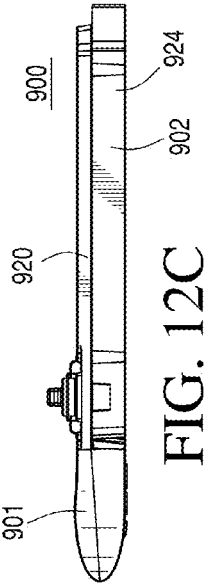

METHOD FOR DETECTING A TARGET ANALYTE THAT EXHIBITS PROTEASE ENZYME ACTIVITY

CROSS-REFERENCE TO RELATED APPLICATIONS

This application is a divisional application of U.S. patent application Ser. No. 14/206,776, filed Mar. 12, 2014, which claims priority to U.S. Provisional Application No. 61/787,343 filed on Mar. 15, 2013, the entireties of which are incorporated herein by reference.

SEQUENCE LISTING

This application contains a Sequence Listing which has been submitted in ASCII format via EFS-Web and is hereby incorporated by reference in its entirety. Said ASCII copy, created on Sep. 2, 2015, is named 07001US(97861-945045) SL.txt and is 38,069 bytes in size.

FIELD OF THE INVENTION

The present invention relates to genetically engineered enzymes, their manufacture, and their use in qualitative or quantitative assays. More specifically, the present invention relates to a genetically engineered signal transducing molecule used to detect proteases in colorimetric, fluorescent and electrochemical based assays. The present invention may be used for assessing coagulation in blood samples. The present invention may also be used for determining a concentration of proteases found in the complement system cascade, and other biological functions.

BACKGROUND OF THE INVENTION

Protease is any enzyme that conducts proteolysis (or proteolytic degradation). Proteolysis is the breakdown of proteins into smaller polypeptides or amino acids, which generally occurs by the hydrolysis of a peptide bond. Protease activity is associated with the regulation of many cellular processes by activating or deactivating enzymes, transcription factors, and receptors. Proteolysis can therefore be a method of regulating biological processes by turning inactive proteins into active ones. For example, in the blood-clotting cascade an initial event triggers a cascade of sequential proteolytic activation of many specific proteases, resulting in blood coagulation. Further, the complement system of the immune response also involves a complex sequential proteolytic activation and interaction that result in an attack on invading pathogens.

Proteases generally fall into four main mechanistic classes: serine, cysteine, aspartyl and metalloproteases. In the active sites of serine and cysteine proteases, the eponymous residue is usually paired with a proton-withdrawing group to promote nucleophilic attack on a peptide bond. Aspartyl proteases and metalloproteases activate a water molecule to serve as the nucleophile, rather than using a functional group of the enzyme itself. However, the overall process of peptide bond cleaving is essentially the same for all protease classes and includes the protease recognizing a potential cleavage site (i.e., a protease recognition site having a sequence of amino acids recognizable to the protease as a potential cleavage site).

Proteolytic degradation by proteases has been detected by techniques using fluorescence, colorimetry, radioactivity, electrophoretic size separation, and electrochemistry. For example, Ionescu et al. (2006, Analytical Chemistry, 78:6327-31) describes the use of a glucose oxidase inner layer encased in a gelatinous polymer. The proteolytic degradation of the gelatinous polymer permitted the release of glucose oxidase, which in the presence of glucose generated detectable hydrogen peroxide. For example, the hydrogen peroxide could be electrooxidized to generate an amperometric signal at a sensor. However, this system suffers from having few gelatinous polymers useful for this assay. In particular, it would be necessary to identify a gelatinous polymer with a useful proteolytic cleavage recognition site.

Wu et al. (2012, Analyst, 137:4829-33) describes the use of a synthetic peptide containing a protease recognition sequence with a terminal biotin at one end, which was covalently bound to an electrode surface, to detect proteolytic degradation. The synthetic peptide was sequentially contacted with a sample containing a protease and Streptavidin-Alkaline Phosphatase. A reduction in signal of the phosphate cleaved substrate generated an electrochemical signal indicating the amount of protease activity.

Additionally, matrix metaloproteinases (MMPs) have been detected electrochemically by Shin et al. (2012, Analytical Chemistry, 85:220-7) by using a terminal Cys peptide covalently assembled onto a gold electrode surface, and having a methylene blue redox label at the other terminal end of the peptide. This synthetic oligopeptide is then subjected to proteolytic cleavage from a sample. The loss of signal predicts the level of protease activity present.

However, these existing assays for proteolytic enzymes lack the ability to generate a positive signal. A positive signal is needed for highly sensitive assays that can detect the lowest levels of disease markers with greater accuracy by amplifying the positive detection signal. Based on the foregoing, there remains a need for systems and methods to detect proteases as useful sensors for clinical diagnosis in a manner that may be amplified.

SUMMARY OF THE INVENTION

The present disclosure provides methods of increasing the sensitivity of assays for proteases by amplifying detection signals, with implications for the development of highly sensitive point-of-care diagnostic systems, e.g., the i-STAT® system. Other objects, advantages and inventive features will become apparent from the detailed description provided herein.

In one embodiment, the present invention is directed to a protein molecule including a protein coding sequence for a starting oxidase enzyme. The protein molecule further includes a substitute protease cleavage recognition sequence, which is a replacement for at least one proteolytic cleavage site of the starting oxidase enzyme. The protein molecule exhibits increased catalytic activity over that of the starting oxidase enzyme upon proteolytic cleavage of the substitute protease cleavage recognition sequence.

In some aspects, the starting oxidase enzyme is L-glutamate oxidase. In some embodiments, the starting oxidase enzyme is configured to convert a cognate substrate into at least hydrogen peroxide.

In another embodiment, the present invention is directed to a hybrid glutamate oxidase enzyme including an amino acid sequence for a starting glutamate oxidase enzyme. The hybrid glutamate oxidase enzyme further includes a foreign protease cleavage recognition sequence, which is a replacement for at least one proteolytic cleavage site of the starting glutamate oxidase enzyme. The hybrid glutamate oxidase enzyme exhibits increased catalytic activity over that of the starting glutamate oxidase enzyme upon cleavage of the foreign protease cleavage recognition sequence.

In some aspects, the foreign protease cleavage recognition sequence is a recognition sequence for thrombin. In some embodiments, the foreign protease cleavage recognition sequence is a recognition sequence for complement C1r subcomponent (C1r).

In another embodiment, the present invention is directed to a synthetic enzyme that is a mutant of wild-type glutamate oxidase. The synthetic enzyme comprises at least one proteolytic cleavage site mutation as compared to the wild-type glutamate oxidase.

In some aspects, the at least one proteolytic cleavage site mutation comprises replacement of at least one wild-type glutamate oxidase proteolytic cleavage recognition sequence with a foreign proteolytic cleavage recognition sequence.

In some aspects, the wild-type glutamate oxidase is produced by genus *Streptomyces*. In some embodiments, the at least one proteolytic cleavage site mutation comprises replacement of at least one wild-type *Streptomyces* glutamate oxidase proteolytic cleavage recognition sequence with a foreign proteolytic cleavage recognition sequence.

In another embodiment, the present invention is directed to a genetically engineered deoxyribonucleic acid (DNA) sequence including a nucleotide sequence encoding a mutant oxidase enzyme for expression in a host. The mutant oxidase enzyme has at least one proteolytic cleavage site mutation as compared to a corresponding wild-type oxidase enzyme. The mutant oxidase enzyme exhibits increased catalytic activity over that of the corresponding wild-type oxidase enzyme upon cleavage of the at least one proteolytic cleavage site mutation.

In another embodiment, the present invention is directed to a unicellular host comprising a genetically engineered DNA sequence comprising a nucleotide sequence encoding a mutant oxidase enzyme for expression in the unicellular host. The mutant oxidase enzyme has at least one proteolytic cleavage site mutation as compared to a corresponding wild-type oxidase enzyme. The mutant oxidase enzyme exhibits increased catalytic activity over that of the corresponding wild-type oxidase enzyme upon cleavage of the at least one proteolytic cleavage site mutation.

In another embodiment, the present invention is directed to a method for detecting a target analyte that exhibits protease enzyme activity. The method includes contacting a sample with a hybrid oxidase enzyme engineered to exhibit increased catalytic activity over that of a starting oxidase enzyme upon cleavage of a mutated protease cleavage recognition sequence, wherein the mutated protease cleavage recognition sequence is a recognition sequence specific for the target analyte. The method further includes contacting a substrate with the engineered hybrid oxidase enzyme, wherein the substrate comprises a cognate composition of matter to the engineered hybrid oxidase enzyme, and the engineered hybrid oxidase enzyme is configured to catalyze conversion of the cognate composition of matter into a detectable product upon proteolytic cleavage of the mutated protease cleavage recognition sequence by the target analyte. The method further includes generating a detectable signal related to the detectable product.

In some aspects, the starting oxidase enzyme is a wild-type glutamate oxidase produced by genus *Streptomyces*. In some embodiments, the target analyte is selected from the group consisting of: thrombin, Factor Xa, Matrix metalloproteinases (MMP), Aminopeptidases, Aggrecanases, Serine Proteases, Tissue Factor-Factor VIIa (TF-FVIIa), Factor VII (FVII), Factor XIa (FXIa), and proteases of the complement system.

In another embodiment, the present invention is directed to a device for detecting a target analyte that exhibits protease enzyme activity. The device includes a conduit configured to accept a sample comprising the target analyte. The device further includes a test region in communication with the conduit, the test region comprising an immobilized hybrid oxidase enzyme engineered to exhibit increased catalytic activity over that of a starting oxidase enzyme upon cleavage of a mutated protease cleavage recognition sequence, wherein the mutated protease cleavage recognition sequence is a recognition sequence specific for the target analyte. The device further includes a substrate region in communication with the test region, the substrate region comprising a substrate comprising a cognate composition of matter to the engineered hybrid oxidase enzyme. The engineered hybrid oxidase enzyme is configured to catalyze conversion of the cognate composition of matter into a detectable product upon proteolytic cleavage of the mutated protease cleavage recognition sequence by the target analyte.

In some aspects, the test region further comprises an electrochemical detection system, a colorimetric detection system, or a fluorescent detection system configured to generate a detectable signal related to the detectable product. In some embodiments, the hybrid oxidase enzyme is immobilized on beads microdispensed within the test region.

In another embodiment, the present invention is directed to a method of preparing a mutant oxidase enzyme. The method includes preparing a genetically engineered deoxyribonucleic acid (DNA) sequence within an expression vector, the genetically engineered DNA sequence comprising: (i) a nucleotide sequence encoding the mutant oxidase enzyme, which has at least one mutated protease cleavage recognition sequence as compared to a corresponding wild-type oxidase enzyme, (ii) an inducible transcriptional promoter, and (iii) a protein tag. The method further includes introducing the expression vector into a host for expression of the genetically engineered DNA sequence to the mutant oxidase enzyme. The mutant oxidase enzyme exhibits increased catalytic activity over that of the wild-type oxidase enzyme upon cleavage of the at least one mutated protease cleavage recognition sequence.

In some aspects, the at least one mutated protease cleavage recognition sequence is a recognition sequence specific for a target analyte.

BRIEF DESCRIPTION OF THE DRAWINGS

The present invention will be better understood in view of the following non-limiting figures, in which:

FIGS. 12A-12E show top, bottom, side, and perspective views of an biosensor cartridge in a closed position in accordance with some aspects of the invention.

DETAILED DESCRIPTION OF THE INVENTION

Introduction

Figure 1:
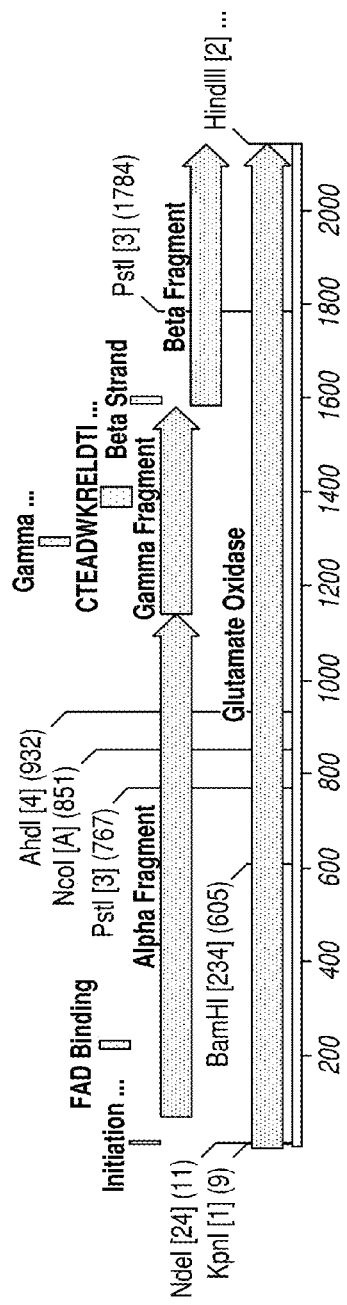
FIG. 1 shows a restriction map for a recombinant DNA sequence comprising "CTEADWKRELDTI" as SEQ ID NO: 12 in accordance with some aspects of the invention.

The present invention is generally applicable to proteins, and more specifically directed to genetically engineered proteins, e.g., enzymes, and the use thereof in qualitative and quantitative assays. Examples of proteins other than enzymes are heme proteins, carrier and receptor proteins. Any protein that can be genetically engineered to accept an inserted or replacement foreign amino acid moiety and the subsequent cleaving of the protein by a cleaving molecule to affect changes of the genetically engineered protein can be utilized. According to the present invention, enzymes of preferably high protein stability and high catalytic activity can be used as the "starting" enzymes for their modification into hybrid enzymes. Starting enzymes can be natural enzymes, enzymatically-inactive fragments of the natural enzymes, or genetically engineered enzymes. Starting enzymes can be in the form of polypeptides. Starting enzymes may include, but are not limited to, glucose oxidase; xanthine oxidase; glutamate oxidase; gulonolactone oxidase; and the like.

The present invention utilizes the replacement or insertion of a foreign or substitute amino acid moiety into an amino acid sequence of a starting protein (e.g., the starting enzyme). The foreign or substitute amino acid moiety serves as a cleavage recognition site for a cleaving molecule (e.g., a protease molecule) and upon being cleaved by the cleaving molecule, a change in the enzymatic activity of the genetically engineered protein is measured. For the hybrid enzyme, in one embodiment of this invention, to be suitable for a qualitative or quantitative assay, the hybrid enzyme should meet the following criteria: (1) the foreign amino acid moiety replaces or is inserted into an amino acid sequence of the starting enzyme and does not appreciably destroy the enzymatic activity of the resultant hybrid enzyme; (2) the foreign amino acid moiety in the resultant hybrid enzyme can still be recognized as cleavage site; and (3) when the cleaving molecule cleaves the cleavage site of the hybrid enzyme, the cleaving molecule modulates (e.g., increases) the enzymatic activity of the hybrid enzyme.

More specifically, the present invention describes the design of a recombinant oxidase gene (e.g., a sequence of nucleotides) and resultant oxidase protein structure (e.g., a sequence of amino acids) thereof. In some embodiments, the gene and protein structure are engineered such that the oxidase exhibits a low enzyme activity in its intact form (e.g., an in-active enzyme precursor form), and exhibits increased enzyme activity over that of the intact form after proteolytic cleavage. For example, the genetically engineered oxidase enzyme exhibits increased catalytic activity over that of a starting oxidase enzyme upon proteolytic cleavage of a substitute protease cleavage recognition sequence.

In some embodiments, the substitute protease cleavage recognition sequence is engineered specific for a target analyte (e.g., a target protease enzyme of the coagulation cascade such as thrombin) such that the increased enzyme activity of the genetically engineered oxidase enzyme is directly related to the protease enzyme activity of the target analyte. Therefore, the increased enzyme activity of the genetically engineered oxidase enzyme may be used to qualitatively or quantitatively determine the presence and/or concentration of the target analyte in a sample. Advantageously, the genetically engineered oxidase enzyme may be used in a colorimetric, fluorescent, or electrochemical assay to measure the increased catalytic activity over that of the starting oxidase enzyme. Even more advantageously, the signal generated from the increased catalytic activity is a positive signal and may be amplified to increase the sensitivity of the assays.

The present invention is discussed hereinafter with respect to a mutated or hybrid glutamate oxidase gene and resultant hybrid glutamate oxidase protein structure engineered to exhibit a low enzyme activity in its intact form, and exhibit increased enzyme activity over that of the intact form after proteolytic cleavage. More specifically, a mutated or hybrid glutamate oxidase gene and resultant glutamate oxidase protein structure is engineered comprising at least one potential Factor Xa or thrombin proteolytic recognition site. However, it should be understood by one skilled in the art that aspects of the present invention may be implemented using any hybrid oxidase gene and resultant hybrid oxidase protein structure (e.g., glucose oxidase) comprising any foreign or substitute proteolytic recognition site.

An oxidase is any enzyme that catalyzes an oxidation-reduction reaction involving molecular oxygen ($O_2$) as the electron acceptor. In these reactions, oxygen is reduced to water ($H_2O$) or hydrogen peroxide ($H_2O_2$). For example, glutamate oxidase [GLOX] (EC 1.4.3.11) is an enzyme that catalyzes the conversion of L-glutamate to detectable hydrogen peroxide in the following reaction:

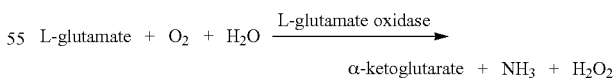

$$\text{L-glutamate} + O_2 + H_2O \xrightarrow{\text{L-glutamate oxidase}} \alpha\text{-ketoglutarate} + NH_3 + H_2O_2$$

A biosensor comprising glutamate oxidase (e.g., an amperometric sensor) may be configured to measure the changes in the current on the working electrode due to direct oxidation of the L-glutamate. Alternatively, the generated hydrogen peroxidase may be detected using an appropriate dye (e.g., tetramethyl benzidine (TMB) with horseradish peroxidase). Consequently, this principle reaction catalyzed by L-glutamate oxidase may be useful for measuring L-glutamate or L-glutamate oxidase enzyme activity.

Chen et al., (2001, Canadian Journal of Microbiology, 47:269-75) discusses the GLOX gene (EC 1.4.3.11) from *Streptomyces platensis*. The gene is coded by 2130 base pairs (710 codons). More specifically, the gene is expressed as a 78 KDa polypeptide, which is the precursor (e.g., a starting structure that exhibits a low enzyme activity), for active extracellular GLOX (an active structure that exhibits increased enzyme activity). Active GLOX has three subunits, alpha, beta and gamma of 39, 19, and 16 KDa, respectively. Arima et al. (2003, Journal of Biochemistry, 134: 805-12) confirmed that metalloendopeptidase (i.e., a protease) from *Streptomyces griseus* (sgmp) may be utilized to cleave the 78 KDa polypeptide precursor of active GLOX into the three subunits comprising active GLOX. Arima demonstrated that the sgmp-treated recombinant GLOX had nearly the same enzymatic activity as compared to active GLOX isolated from *Streptomyces* sp. X-119-6, and suggested that the proteolytic cleavage by metalloendopeptidase both increased the catalytic rate of GLOX and stabilized the protein.

In some embodiments of the invention, the proteolytic cleavage recognition sites (e.g., the sequence of amino acids) used by metalloendopeptidase to recognize cleavage sites to generate the active GLOX comprising the subunits alpha, beta and gamma are replaced with foreign or substitute cleavage recognition sites designed for specific proteases of interest in assessing biological functions. For example, in one embodiment, the substitute protease cleavage recognition sequence may be a recognition sequence for thrombin, which may be used to assess the coagulation functions of a patient. Therefore, the direct relationship between cleavage of the GLOX molecule into the three subunits by a protease and resultant increase in enzymatic activity enables the GLOX enzymatic activity to be associated with the presence of proteases in a test sample. Specifically, the activated GLOX has increased catalytic capability to generate hydrogen peroxide, which can be utilized to determine qualitatively or quantitatively the presence or concentration of a proteolytic enzyme (i.e., a protease) in a sample.

A Hybrid Protein Molecule Comprising a Foreign Amino Acid Moiety

One example of a genetically engineered protein can be a hybrid enzyme. For example, amino acid sequences (e.g., an amino acid moiety or function group) can be inserted into an amino acid sequence of a starting protein/enzyme to create a hybrid enzyme comprising the starting amino acid sequence and the inserted amino acid sequence. In some embodiments, construction of a genetically engineered enzyme may comprise inserting the amino acid moiety comprising at least one substitute cleavage recognition site into an amino acid sequence of a starting enzyme such that a hybrid enzyme is created comprising the at least one substitute cleavage recognition site. The at least one substitute cleavage recognition site may be designed to be selective for a target analyte (e.g., a protease of diagnostic significance). For example, an assay in accordance with some aspects of the invention may comprise a hybrid enzyme engineered to detect the presence or concentration of a protease such as thrombin. Specifically, the hybrid enzyme may be constructed by replacing amino acid sequences of the starting enzyme comprising a proteolytic cleavage site with a sequence of amino acids comprising a foreign proteolytic cleavage site recognized specifically by thrombin (e.g., the proteolytic recognition sequence of A-B-Pro-Arg|X-Y, where A and B are hydrophobic amino acids and X and Y are nonacidic amino acids, or Gly-Arg|-Gly (as described by Sigma at <http://www.sigmaaldrich.com/life-science/metabolomics/enzymeexplorer/analytical-enzymes/thrombins.html>) referencing Chang, 1985, European Journal of Biochemistry, 151:217-224e).

Generally, a foreign amino acid moiety, such as a substitute cleavage recognition site, can replace or be inserted into an amino acid sequence of a starting protein as follows. The gene for the starting protein may be cloned into an expression plasmid. This may be accomplished by using a polymerase chain reaction ("PCR") to amplify the deoxyribonucleic acid (DNA) sequence of the gene from the native source of the enzyme, either a procaryotic or eucaryotic organism (e.g., wild-type glutamate oxidase produced by genus *Streptomyces*). The PCR amplification procedure utilizes knowledge of either partial amino acid sequence of the protein or partial nucleotide sequence of the gene or flanking sequences. The gene may also be obtained by direct chemical synthesis of the DNA encoding the protein. However, this requires knowledge of either the complete protein sequence or the complete nucleotide sequence of the gene. Once the gene is cloned into a plasmid, the entire nucleotide sequence can be obtained by DNA sequencing and the protein may be expressed by introducing the plasmid into a compatible host, e.g., bacterial, yeast or mammalian cells.

If the 3-dimensional (3D) structure of the enzyme is known, sites of the starting enzyme (e.g., already present cleavage recognition sites) may be chosen for receiving insertion or replacement with the substitute cleavage recognition site. From the nucleotide sequence of the gene, restriction fragment replacements are designed to construct a gene encoding the desired hybrid enzyme comprising at least one substitute cleavage recognition site. If the structure of the enzyme is not known, at least one substitute cleavage recognition site can replace or be inserted into amino acid sequences of the starting enzyme randomly throughout the protein and the resultant hybrid enzyme-substitute cleavage recognition site may be screened for increased enzymatic activity upon cleavage of the substitute cleavage recognition site. The random substitute cleavage recognition site that replaces or is inserted into amino acid sequences of the starting enzyme can be done with the appropriate DNA fragment at restriction sites in the gene.

In one embodiment of the present invention, L-glutamate oxidase (e.g., wild-type glutamate oxidase found in genus *Streptomyces*) may be modified or mutated into a hybrid enzyme configured to exhibit increased catalytic activity over that of the starting L-glutamate oxidase upon proteolytic cleavage of at least one substitute protease cleavage recognition sequence by a cleaving molecule. The cleaving molecule may be an analyte that exhibits diagnostic significance, such as proteases (e.g., thrombin). Therefore, in some embodiments, the at least one substitute protease cleavage recognition sequence may be engineered specific to a target analyte such as thrombin, Factor Xa, Matrix metalloproteinases (MMP), Aminopeptidases, Aggrecanases, Serine Proteases, Tissue Factor-Factor VIIa (TF-FVIIa), Factor VII (FVII), Factor Xia (FXIa), or proteases of the complement system (e.g., complement C1r subcomponent).

For example, SEQ ID NO:1 describes the recombinant DNA and SEQ ID NO:7 describes the protein coding sequence (e.g., an amino acid sequence) based on the wild type GLOX protein sequence from *Streptomyces platensis* (Q9AIT1 www.uniprot.org). A restriction map for this DNA sequence is shown in FIG. 1. The gene for the starting wild type GLOX protein sequence may be cloned into an expression vector (e.g., a plasmid such as pET45b(+) or a virus) at the KpnI/HindIII site, the expression vector may be transformed or introduced into a compatible host (e.g., BL21 (DE3) *E. coli* for use with bacteriophage T7 promoter-based expression systems), and over expressed using isopropyl β-D-1-thiogalactopyranoside (IPTG) induction. The expressed protein with an associated protein tag (e.g., a hexahistidine polypeptide tag (SEQ ID NO: 11)) may be column purified on a column (e.g., a nickel column) to near homogeneity.

In alternative embodiments, SEQ ID NO: 5 describes the recombinant DNA and SEQ ID NO: 9 describes the protein coding sequence (e.g., an amino acid sequence) based on another wild type GLOX with NdeI and EcoRI recognition sequences at the 5'-end and XhoI and EcoRV recognition sequences at the 3'-end. This recombinant DNA may be cloned into an expression vector (e.g., pET28b+) at the EcoRI/XhoI sites in a similar manner discussed with respect to SEQ ID NO: 1. Additionally, this recombinant DNA mat be cloned into pMAL-c5X and pMAL-p5X at the NdeI and EcoRV sites.

Figure 2:
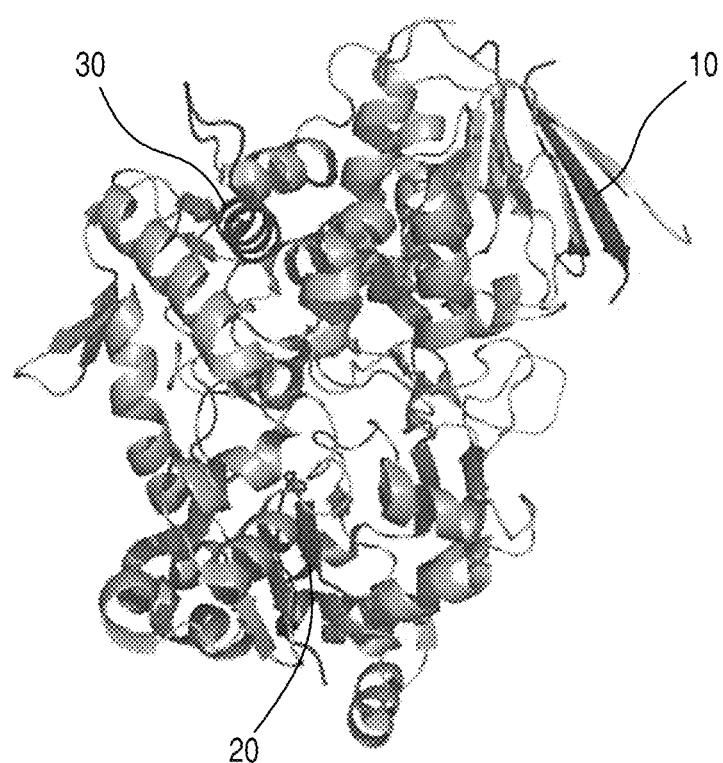
FIG. 2 shows an X-ray crystallograph depiction of a wild type GLOX protein sequence in accordance with some aspects of the invention.

FIG. 2 shows an X-ray crystallograph depiction of the wild type GLOX protein sequence having a folded structure based on data found in the PDB database for 2E1M (from *Streptomyces* sp X-119-6). In this model, *Streptomyces griseus* (sgmp) endoproteolytic cleavage sites 10, 20, and 30 are identifiable on the external portion of the molecule, and may be chosen for replacement with a substitute cleavage recognition site. SEQ ID NO: 2 describes the *Streptomyces griseus* (sgmp) endoproteolytic cleavage sites 10, 20, and 30. From the nucleotide sequence of the wild type GLOX gene, restriction fragment replacements are designed to construct a gene encoding the desired hybrid oxidase enzyme comprising the at least one substitute cleavage recognition site as a replacement for the at least one of *Streptomyces griseus* (sgmp) endoproteolytic cleavage sites 10, 20, and/or 30. SEQ ID NO: 3 describes a Factor Xa proteolytic cleavage site, which may be used as a substitute for the *Streptomyces griseus* (sgmp) proteolytic cleavage sites (SEQ ID NO: 2).

Figure 3:
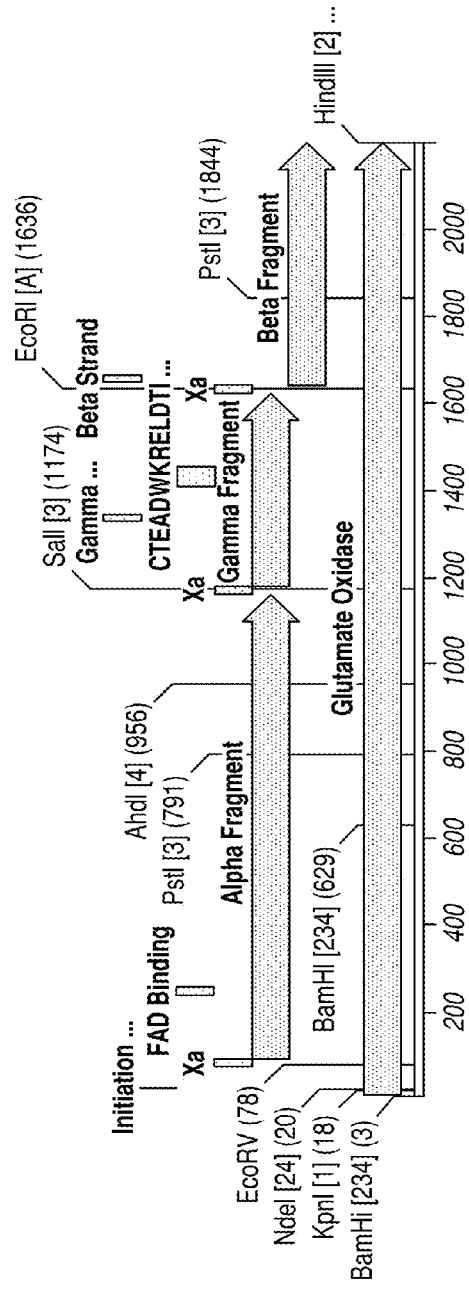
FIG. 3 shows a restriction map with various features of a Factor Xa modified recombinant DNA sequence comprising "CTEADWKRELDTI" as SEQ ID NO: 12 in accordance with some aspects of the invention.

In some embodiments, similar to the recombinant wild-type sequence described above, SEQ ID NO: 4 describes the DNA and SEQ ID NO: 8 describes the protein coding sequence (e.g., an amino acid sequence) of a Factor Xa modified recombinant GLOX gene version, where at least one of the sgmp cleavage sites in the wild type GLOX protein sequence is replaced with a Factor Xa recognition sequence. Factor Xa catalyzes the conversion of prothrombin to thrombin in conjunction with other cofactors. More specifically, Factor Xa is activated from Factor X by both Factor IX (with its cofactor, Factor VIII in a complex known as intrinsic Xase) and Factor VII with its cofactor, tissue factor (a complex known as extrinsic Xase) and may be used in analytical testing to monitor heparin levels in a patient. FIG. 3 shows a restriction map with various features of the Factor Xa modified recombinant sequence. As described above, this DNA may be sub-cloned into an expression vector (e.g., a plasmid such as pET45b(+) or a virus) at the BamHI/HindIII site, the expression vector may be transformed or introduced into a compatible host (e.g., BL21 (DE3) *E. coli* for use with bacteriophage T7 promoter-based expression systems), and over expressed using IPTG induction. The expressed hybrid protein with an associated protein tag (e.g., a hexahistidine polypeptide tag (SEQ ID NO: 11)) may be column purified on a column (e.g., a nickel column) to near homogeneity.

In alternative embodiments, SEQ ID NO: 6 describes the DNA and SEQ ID NO: 10 describes the protein coding sequence (e.g., an amino acid sequence) of a Factor Xa modified recombinant GLOX gene version, where at least one of the sgmp cleavage sites in the wild type GLOX protein sequence is replaced with a Factor Xa recognition sequence. As described above with respect to SEQ ID NO: 4, this DNA may be sub-cloned into an expression vector (e.g., a plasmid such as pET45b(+) or a virus).

Accordingly, in some embodiments, the present invention is directed to a genetically engineered DNA sequence comprising a nucleotide sequence encoding a mutant oxidase enzyme for expression in a host. The mutant oxidase enzyme has at least one proteolytic cleavage site mutation as compared to a corresponding wild-type oxidase enzyme, and the mutant oxidase enzyme is engineered to exhibit increased catalytic activity over that of the corresponding wild-type oxidase enzyme upon cleavage of the at least one proteolytic cleavage site mutation.

The genetically engineered DNA sequence for the mutant oxidase enzyme may comprise: (i) a nucleotide sequence encoding the mutant oxidase enzyme, which has at least one mutated protease cleavage recognition sequence as compared to a corresponding wild-type oxidase enzyme, (ii) an inducible transcriptional promoter, and (iii) a protein tag. In additional or alternative embodiments, the protein tag may be a fused compatible purification tag such as a hexahistidine tag (SEQ ID NO: 11) and a maltose fusion tag. One of ordinary skill in the art should understand the processes for adding the inducible transcriptional promoter and the protein tag to the nucleotide sequence encoding the mutant oxidase enzyme such that further discussion of those processes is unnecessary.

In additional embodiments, the present invention is directed to a unicellular host (e.g., BL21(DE3) *E. coli*) comprising the genetically engineered DNA sequence comprising the nucleotide sequence encoding the mutant oxidase enzyme for expression in the unicellular host. The mutant oxidase enzyme has at least one proteolytic cleavage site mutation as compared to a corresponding wild-type oxidase enzyme, and the mutant oxidase enzyme exhibits increased catalytic activity over that of the corresponding wild-type oxidase enzyme upon cleavage of the at least one proteolytic cleavage site mutation.

In some embodiments, the present invention is directed to a protein molecule or hybrid enzyme comprising a protein coding sequence (e.g., an amino acid sequence) for a starting oxidase enzyme and a substitute protease cleavage recognition sequence (e.g., an amino acid moiety), which is a replacement for at least one proteolytic cleavage site of the starting oxidase enzyme. The protein molecule is engineered to exhibit increased catalytic activity over that of the starting oxidase enzyme upon proteolytic cleavage of the substitute protease cleavage recognition sequence. The starting oxidase enzyme should be capable of converting a cognate substrate (e.g., L-glutamate in the instance that the starting enzyme is L-glutamate oxidase) into at least one product that is detectable (e.g., hydrogen peroxide).

Amperometric Electrochemical System for the Detection of a Target Analyte

Figure 4:
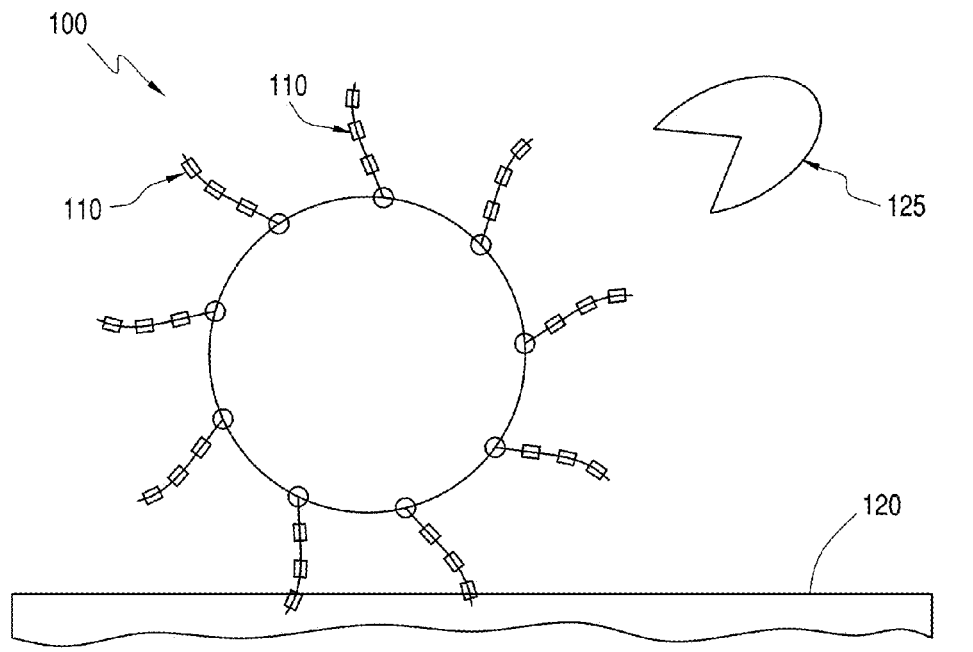
FIG. 4 illustrates the principle of an amperometric electrochemical system in accordance with some aspects of the invention.
Figure 4:
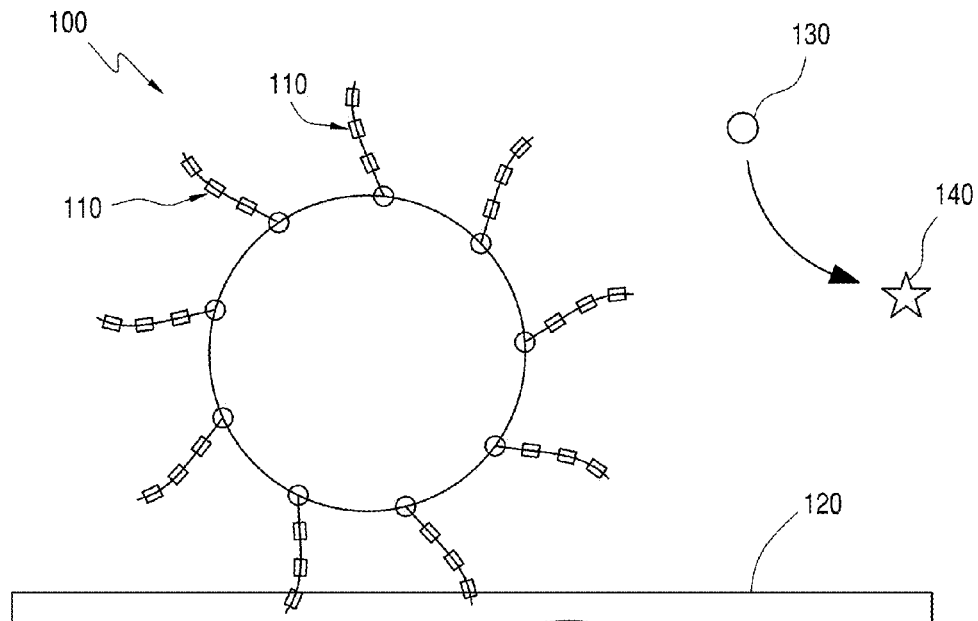

FIG. 4 illustrates the principle of an amperometric electrochemical system 100 according to exemplary embodiments of the present invention for determination of the presence and/or concentration of a target analyte, e.g., thrombin. However, it should be understood that while specific embodiments are described for a thrombin assay, the sensor structure and microparticle reagents described herein may also be useful for detecting Factor Xa, Matrix metalloproteinases (MMP), Aminopeptidases, Aggrecanases, Serine Proteases, Tissue Factor-Factor VIIa (TF-FVIIa), Factor VII (FVII), Factor XIa (FXIa), or proteases of the complement system (e.g., complement C1r subcomponent), among other analytes.

In a first contacting step, a sample, e.g., blood, urine, buccal samples, vaginal swabs, semen, tears, or nasal swabs, may be introduced into a conduit or sample holding chamber of a cartridge of the present invention (e.g., a cartridge as disclosed in U.S. Pat. No. 7,723,099, which is incorporated herein by reference in its entirety) with a fluidics format suitable for an assay. The sample may be moved from the conduit or sample holding chamber into contact with a hybrid protein structure or enzyme 110 as described herein engineered to exhibit increased catalytic activity over that of a starting oxidase enzyme upon cleavage of a mutated protease cleavage recognition sequence.

In some embodiments, the hybrid protein structure or enzyme 110 may be attached on, or close to, at least one amperometric working electrode 120. Accordingly, the at least one amperometric working electrode 120 may be coated with a biolayer comprising a covalently attached hybrid protein structure or enzyme 110. The hybrid protein structure or enzyme 110 is thus immobilized on or in close proximity to the at least one amperometric working electrode 120. The hybrid protein structure or enzyme is depicted in the figures as a linear species; however, it should be understood by those of skill in the art that in reality the hybrid protein structure or enzyme comprises a 3D folded structure, for example as depicted in FIG. 2.

A catalytic region on the at least one amperometric working electrode 120 may be defined by a hydrophobic ring of polyimide or another photolithographically produced layer. A microdroplet or several microdroplets (approximately 5-40 nanoliters in size) containing the hybrid protein structure or enzyme in a substantially inactive form, for example bound to latex microparticles, may be dispensed on the surface of each sensor. The photodefined ring contains this aqueous droplet allowing the hybrid protein structure or enzyme coated region to be localized to a precision of a few microns. The catalytic region may be made from about 0.03-2 mm$^2$ in size. The upper end of this size (e.g., 2 mm$^2$) may be limited by a size of a sensor conduit comprising the sensors in present embodiments, and is not a limitation of the invention.

In the first contacting step, any protease 125 within the sample that recognizes the mutated protease cleavage recognition sequence should be allowed to perform proteolytic degradation (e.g., cleaving at or near the mutated protease cleavage recognition sequence) of the hybrid protein structure or enzyme 110 to convert the hybrid protein structure or enzyme 110 to an active state.

In a second contacting step or analysis step, a cognate composition of matter or substrate 130 is introduced to the active hybrid protein structure or enzyme 110 and the at least one amperometric working electrode 120 such that the active hybrid protein structure or enzyme 110 may convert the substrate to a detectable product 140 (e.g., catalyze the conversion of L-glutamate to detectable hydrogen peroxide). As should be understood, the increased catalytic activity of the active hybrid protein structure or enzyme 110 over that of a starting protein structure or enzyme is related to the protease enzyme activity of the target analyte in the sample. The increased catalytic activity of the active hybrid protein structure or enzyme 110 may be indicative to a concentration or presence of the protease within the sample that recognizes the mutated protease cleavage recognition sequence.

For example, the detectable product 140 may cause an electrical potential to be generated across the at least one amperometric working electrode 120 that in turn generates a signal relative to the electrical potential caused by the detectable product 140. The detectable product 140 generated from the reaction of the active hybrid protein structure or enzyme 110 with the cognate substrate 130 at the at least one amperometric working electrode 120 may be essentially proportional to the protease within the sample.

In exemplary embodiments, the substrate 130 may be comprised of L-glutamate or other suitable material and the detectable product may be hydrogen peroxide or other suitable detectable products. In some embodiments, a detectable signal is generated by the at least one amperometric working electrode 120. However, the present invention is not limited to an amperometric electrochemical system for the detection of a target analyte. For example, in alternative or additional embodiments, the detectable signal may be generated by a colorimetric detection system or a fluorescent detection system.

In some embodiments, the target analyte is a MMP such as MMP1, MMP2, MMP3, MMP3, MMP8, MMP9, MMP13, MMP14, MMP15, MMP16, MMP17, MMP24, tissue inhibitor of metalloproteinases-1 (TIMP1), and TIMP2. In additional or alternative embodiments, the target analyte is an Aminopeptidase such as Aminopeptidase N or Human Dipeptidylpeptidase IV. In additional or alternative embodiments, the target analyte is a protease of the compliment system such as Complement C1r subcomponent (C1r), Complement C1s subcomponent (C1s), or manna-binding lectin serine protease-2 (MASP2). In yet other embodiments, the target analyte is a protease involved in the process of thrombogenesis.

Amperometric Working Electrode Fabrication

Figure 5:
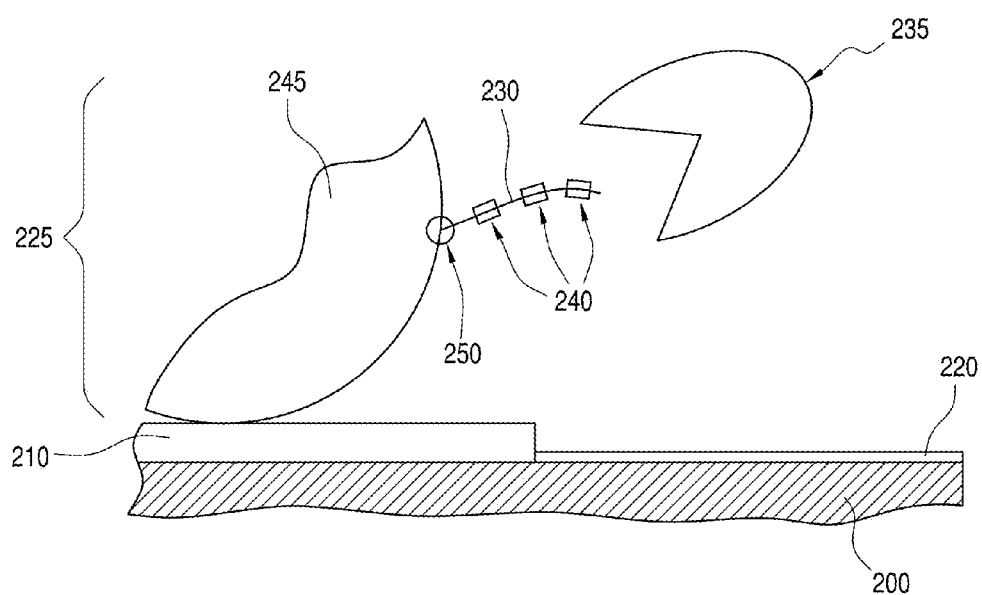
FIG. 5 shows a microfabricated sensor array comprising at least one amperometric working electrode in accordance with some aspects of the invention.

A preferred embodiment of a microfabricated sensor array comprising at least one amperometric working electrode is shown in FIG. 5. In this embodiment, the microfabricated sensor array comprises a pair of biosensors or electrodes comprising a primary sensor or electrode and a reference sensor or electrode. For example, the biosensors or electrodes may be fabricated as adjacent structures, respectively, on a support such as a silicon chip.

The electrodes may be formed on a silicon support having a gold surface coated with a photodefined layer of polyimide. For example, wafer-level microfabrication of a preferred embodiment of the sensor array may be achieved as follows. A planar non-conducting substrate 200 may be used as a base for the sensor array. A conducting layer 210 may be deposited on the substrate 200 by conventional means or microfabrication known to those of skill in the art to form at least one electrode. The conducting layer 210 may comprise a noble metal such as gold or platinum, although other unreactive metals such as iridium may also be used, as many non-metallic electrodes of graphite, conductive polymer, or other materials may also be used.

For example, a base electrode may comprise a square array of 5-10 µm gold disks, e.g., 7 µm gold disks, on 15 µm centers. The array may cover a region, e.g., a circular region, approximately 300 to 900 µm in diameter, optionally 600 µm in diameter, and may be formed by photo-patterning a thin layer of the polyimide of thickness 0.35 µm over a substrate made from a series of layers comprising Si, SiO$_2$, TiW, and/or Au, or combinations thereof. The array of microelectrodes affords high collection efficiency of electroactive species with a reduced contribution from any electrochemical background current associated with the capacitance of the exposed metal. In particular, regularly spaced openings in the insulating polyimide layer define a grid of small gold electrodes at which the p-aminophenol may be oxidized in a 2 electron per molecule reaction.

Microfabrication techniques (e.g. photolithography and plasma deposition) may be utilized for construction of the multilayered sensor structures in confined spaces. For example, methods for microfabrication of the electrochemical biosensors on silicon substrates are disclosed in U.S. Pat. No. 5,200,051, which is hereby incorporated by reference in its entirety. These include dispensing methods, methods for attaching biological reagent, e.g., hybrid enzymes, to surfaces including photoformed layers and microparticle latexes, and methods for performing electrochemical assays.

The microfabricated sensor array may also comprise an electrical connection 220 and a biolayer 225 (as discussed above with respect to FIG. 4), which are deposited onto at least a portion of the conducting layer 210 and/or the non-conducting substrate 200. In the present invention, the biolayer 225 may include a porous layer comprising a surface with a sufficient amount of a molecule 230 (e.g., the immobilized hybrid enzyme) that may be cleaved by an analyte of interest 235 at least one proteolytic cleavage site 240, and respond to the presence of a substrate by producing a change that is capable of measurement.

Optionally, a permselective screening layer may be interposed between the conducting layer 210 and the biolayer 225 to screen electrochemical interferents as described in U.S. Pat. No. 5,200,051, which is hereby incorporated by reference in its entirety. In particular, the electrodes described herein may be manufactured to optimize a signal-to-noise ratio, or amperometric background signal. For example, an intervening polyvinyl alcohol (PVA) layer of about 0.5-5.0 μm thickness (preferably 0.6-1.0 μm) may be placed between the electrodes and the biolayer or hybrid enzyme reagent layer significantly attenuating the background component, as described in U.S. Pat. No. 7,723,099, which is hereby incorporated by reference in its entirety. An advantage of PVA as the background-reducing layer is that noise is reduced without appreciably affecting the Faradaic component of the signal. While the PVA layer reduces the diffusion coefficient of small molecules by about 50% it has been found that it does not change the current at the coated electrodes, for two reasons. First, with PVA layers of about 1 micron thickness, the detected electroactive species is present in a diffusion layer of at least ten times that thickness, so there is little decrease in transport due to the PVA layer. Second, a steady-state current is measured in the biosensor, which is effectively independent of the transport rate and electrode kinetics, but is a function of the enzymatic rate of production of the detectable species, such as hydrogen peroxide generated from L-glutamate by the enzyme L-glutamate oxidase.

The porous PVA layer may be prepared by spin-coating an aqueous mixture of PVA plus a stilbizonium photoactive, cross-linking agent over the microelectrodes on the wafer. The spin-coating mixture optionally includes bovine serum albumin (BSA). The spin-coating mixture may then be photo-patterned to cover only a region above and around the sensor arrays, and preferably has a thickness of about 0.6 μm.

In specific embodiments, the biolayer 225 may be formed from polystyrene or latex beads 245 of specific diameter in the range of about 0.01 to 5.0 μm. The beads may be modified by covalent attachment of any suitable molecule consistent with the above definition of the biolayer (as discussed in further detail below). Many methods of attachment exist in the art, including providing amine reactive N-hydroxysuccinimide ester groups for the *facile* coupling of lysine or N-terminal amine groups of proteins. In specific embodiments, the microparticle 240 may be coated with nickel and use a hexahistidine tag 250 ("hexahistidine" disclosed as SEQ ID NO: 11) on the molecule to bind, and the molecule may be a hybrid enzyme engineered for cleaving by one or more proteases 235 in a sample.

In one embodiment, the biolayer 225 comprising microparticle beads 240 having surfaces that are covalently modified by a suitable molecule, may be affixed to the sensors by the following method. A microdispensing needle may be used to deposit onto a surface of the electrode or a photo-patterned PVA permselective layer covering the electrode a small droplet of the microparticle reagents. Specifically, in order to bind the microparticle reagents to the electrode, a droplet of about 0.4 nL comprising about 1% solids (i.e., the microparticles) in 0.08% Tween 20 may be microdispensed (e.g., using the method and apparatus of U.S. Pat. No. 5,554,339, which is incorporated herein by reference in its entirety) onto a surface of the electrode or a photo-patterned PVA permselective layer covering the electrode. The droplet may then be allowed to dry. The adherence of the dried microparticles particles to the porous layer substantially prevents dissolution of the microparticles into the sample (e.g., the blood sample). However, in some embodiments additional coupling chemistry may be used to ensure bead immobilization on the porous layer and/or the biosensors. Such techniques are well known in the art.

Microparticle Reagent Fabrication

In some embodiments, microparticles (e.g., carboxylate-modified latex microparticles supplied by Bangs Laboratories Inc. or Seradyn Microparticles Inc.) coated with hybrid enzymes may be prepared for use in detecting target analytes such as thrombin in accordance with some aspects of the present invention. For example, the microparticles may first be buffer exchanged by centrifugation, and then the hybrid enzymes may be added to the microparticles (e.g., the hybrid enzymes may be allowed to passively adsorb onto the microparticles). Inactive groups (e.g., carboxyl groups) on the microparticles may then be activated to form amide bonds to the hybrid enzymes. Microparticle aggregates may then be removed by centrifugation and the finished microparticles may be stored frozen for future use with the systems and devices of the present invention.

System Comprising a Sensor Array Configured for Target Analyte Detection

Figure 6:
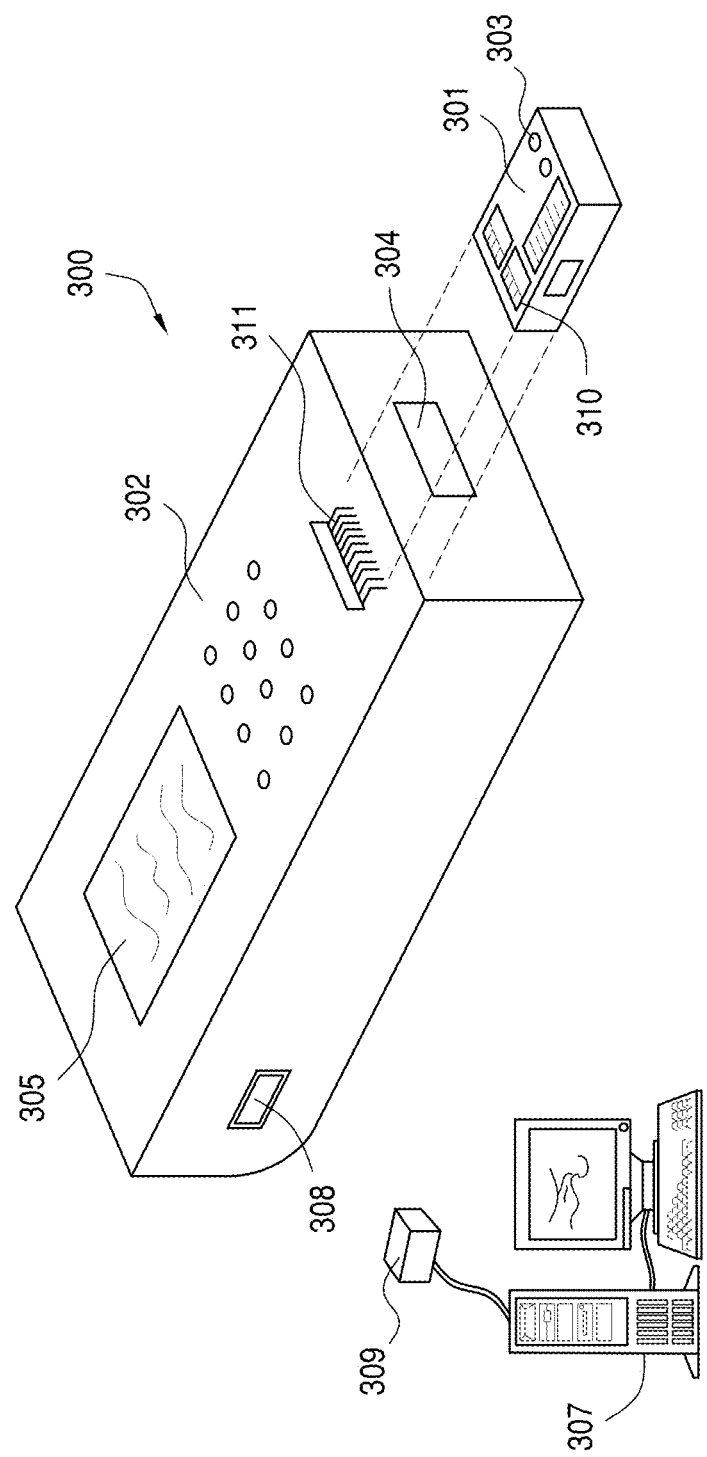
FIG. 6 shows an isometric view of a disposable sensing device and reader device in accordance with some aspects of the invention.

Referring to FIG. 6, the system 300 of the present invention may comprise a self-contained disposable sensing device or cartridge 301 and a reader device or instrument 302. A fluid sample (e.g., whole blood or urine) to be measured is drawn into a sample entry orifice or port 303 in the cartridge 301, and the cartridge 301 may be inserted into the reader device 302 through a slotted opening 304. The reader device 302 may comprise a processor configured to perform measurements of analyte concentration within the fluid sample, as discussed herein in further detail. Measurements and determinations performed by the reader may be output to a display 305 or other output device, such as a printer or data management system 307 via a port on the reader 308 to a computer port 309. Transmission can be via Wifi, Bluetooth link, infrared and the like. Note that where the sensors are based on electrochemical principles of operation, the sensors 310 (e.g., a primary sensor and optionally a reference sensor) in the cartridge 301 make electrical contact with the instrument 302 via an electrical connector 311. For example, the connector may be of the design disclosed in jointly owned U.S. Pat. No. 4,954,087, incorporated herein by reference in its entirety. The instrument 302 may also include a method for automatic fluid flow compensation in the cartridge 301, as disclosed in jointly owned U.S. Pat. No. 5,821,399, which also is incorporated herein by reference in its entirety.

Figure 7:
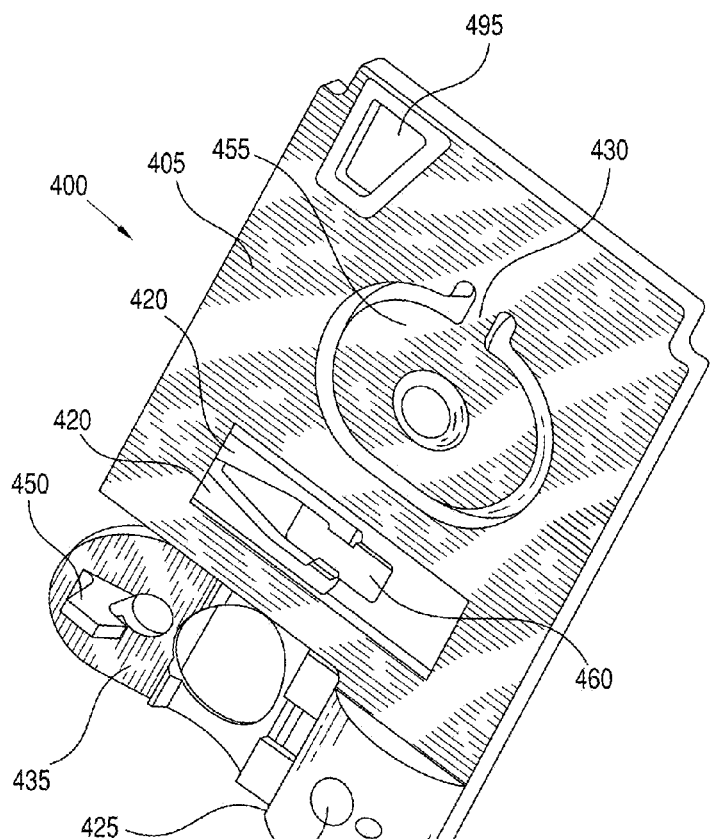
FIG. 7 shows an isometric top view of a biosensor cartridge cover in accordance with some aspects of the invention.
Figure 8:
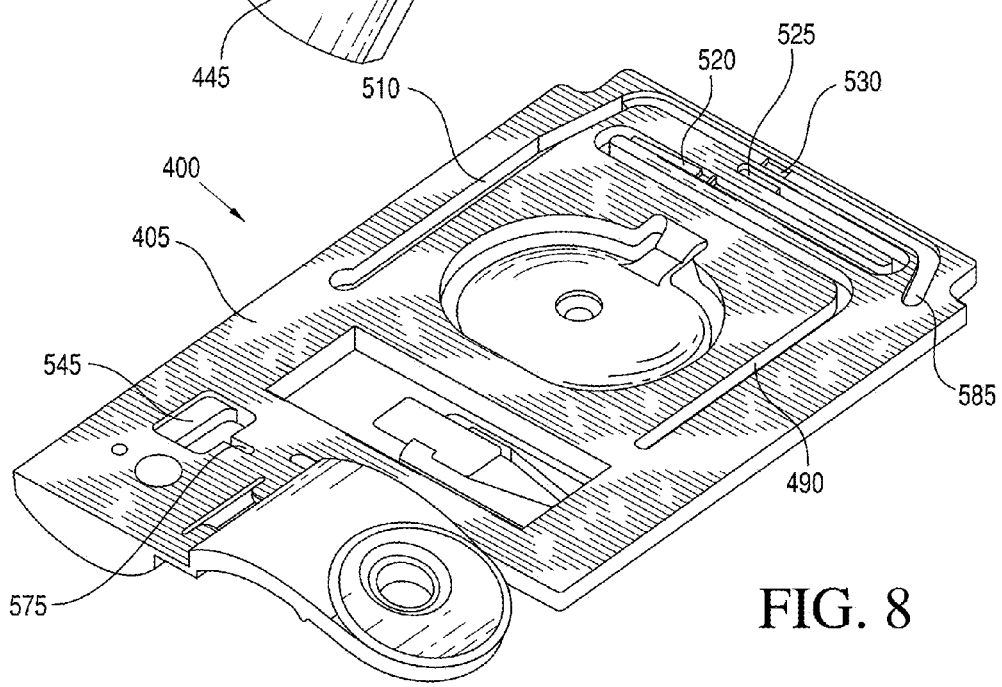
FIG. 8 shows an isometric bottom view of a biosensor cartridge cover in accordance with some aspects of the invention.
Figure 9:
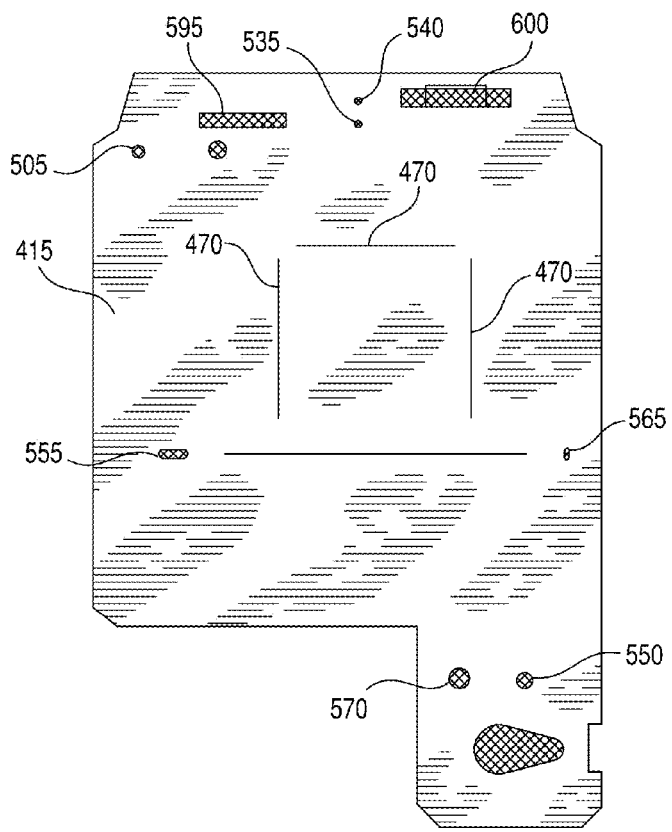
FIG. 9 shows a top view of a tape gasket in accordance with some aspects of the invention.
Figure 10:
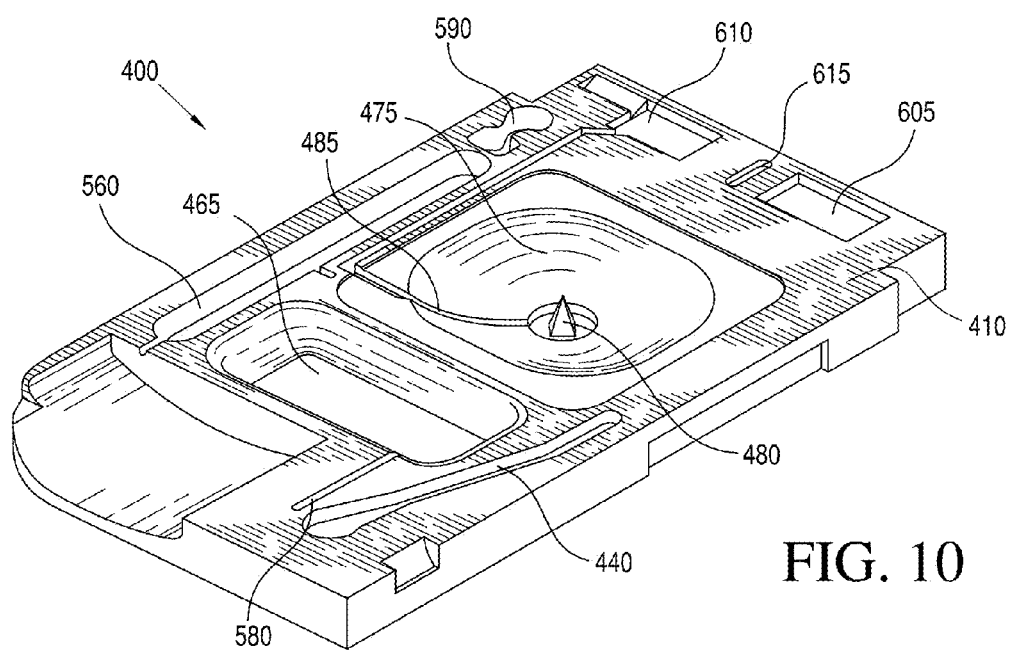
FIG. 10 shows an isometric top view of a biosensor cartridge base in accordance with some aspects of the invention.

In one embodiment, as shown in FIGS. 7-10, a cartridge 400 (e.g., a disposable assay cartridge) may comprise a cover 405 (as shown in FIGS. 7 and 8), a base 410 (as shown in FIG. 10), and a thin-film adhesive gasket 415 (as shown in FIG. 9) that is disposed between the base 410 and the cover 405. The cartridge 400 may be configured for insertion into a reader device, and therefore the cartridge 400 may comprise a plurality of mechanical and electrical connections (not shown) for this purpose. Advantageously, a feature of the cartridge 400 is that once a sample is loaded within the cartridge 400, analysis of the sample may be completed and the cartridge 400 may discarded without an operator or others contacting the sample.

Referring to FIG. 7, the cover 405 may be made of a rigid material, preferably plastic, and capable of repetitive deformation at flexible hinge regions 420, 425, and 430 without cracking. The cover 405 may comprise a lid 435, attached to a main body of the cover 405 by the flexible hinge 425. In operation, after introduction of a sample into a sample holding chamber 440 (as shown in FIG. 10) through a sample entry port 445, the lid 435 may be secured over an entrance to the sample entry port 445, preventing sample leakage. The lid 435 may be held in place by a hook 450.

The cartridge 400 optionally may also have a closure feature as described in jointly owned U.S. Pat. No. 7,682, 833, which is hereby incorporated by reference in its entirety, for sealing the sample entry port 445 in an air-tight manner. This closure device may be slidable with respect to a body of the cartridge 400 and provides a shearing action that displaces excess sample located in the region of the sample entry port 445, reliably sealing a portion of the sample in the sample holding chamber 440 between the sample entry port 445 and a capillary stop. Specifically, the cartridge 400 may be sealed by slidably moving a sealing element over the surface of the cartridge in a manner that displaces excess fluid sample away from the sample entry port 445, seals a volume of the fluid sample within the internal fluid sample holding chamber 440, and inhibits fluid sample from prematurely breaking through the internal capillary stop.

The cover 405 may further comprise two paddles 455 and 460 that are moveable relative to the body of the cover 405, and which are attached to the cover 405 by the flexible hinge regions 420 and 430. The paddle 460 may be configured to be operated by a pumping means such that a force is exerted upon an air bladder comprised of cavity 465 (as shown in FIG. 9) and the gasket 415. Operation of the paddle 460 displaces fluid within conduits of the cartridge 400.

The paddle 455 may be configured to be operated upon by a second pumping means such that a force is exerted upon the gasket 415, which can deform because of slits 470 cut therein (as shown in FIG. 9). Deformation of the gasket 415 may transmit pressure onto a fluid-containing foil pack filled with a fluid, e.g., approximately 130 µL of analysis/wash solution or fluid, located in cavity 475 (as shown in FIG. 10), rupturing the foil pack upon spike 480, and expelling fluid into conduit 485. The conduit 485 may be connected via a short transecting conduit in the base 410 to a conduit 490 (as shown in FIG. 8). The fluid fills a front of the conduit 485 first pushing fluid into a small opening in the gasket 415 that acts as a capillary stop.

Additional action in the cartridge 400 generated by mechanisms within the reading device applied to the cartridge 400 may be used to inject one or more air segments into the fluid at controlled positions within the conduit 490. The air segments may be used to wash a sensor surface of the sensor array and the surrounding conduit 490 with a minimum amount of fluid. For example, the cover 405 may further comprise a hole covered by a thin pliable film 495. In operation, pressure exerted upon the film 495 may expel one or more air segments into the conduit 490 through a small hole 505 in the gasket 415 (as shown in FIGS. 8 and 9).

Referring to FIG. 8, a lower surface of the cover 405 further comprises the conduit 490 and another conduit 510. The conduit 490 includes a constriction 520 that controls fluid flow by providing resistance to the flow of the fluid. Optional coatings 525 and 530, e.g., dry reagent coatings, may provide hydrophobic surfaces on the conduit 510, which together with gasket holes 535 and 540 control fluid flow between conduits 190 and 510. A recess 545 in the base may provide a pathway for air to enter and/or escape the conduit 440 through hole 550 in the gasket.

Referring to FIG. 9, the thin-film gasket 415 comprises various holes and slits to facilitate transfer of fluid and air between conduits within the base 405 and the cover 410, and to allow the gasket 415 to deform under pressure where necessary. Specifically, a hole 555 may permit fluid to flow from the conduit 490 into a waste chamber 560, a hole 565 may comprise a capillary stop between conduits 440 and 510, a hole 570 may permit air to flow between a recess 575 (as shown in FIG. 8) and a conduit 580 (as shown in FIG. 10), the hole 550 provides for air movement between the recess 545 and the conduit 440, and the hole 505 permits fluid to flow from a conduit 585 (as shown in FIG. 8) to the waste chamber 560 via optional closeable valve 590 (as shown in FIG. 10). Holes 595 and 600 permit a plurality of electrodes that are housed within cutaways 605 and 610, respectively, to contact fluid within the conduit 490. In a specific embodiment, cutaway 610 houses a ground electrode, and/or a counter-reference electrode, and cutaway 605 houses at least one analyte sensor, and optionally, a reference sensor.

Referring to FIG. 10, the conduit 440 may be configured as a sample holding chamber that connects the sample entry port 445 to the conduit 510 in the assembled cartridge 400. The cutaway 605 may house at least one analyte sensor (e.g., the pair of electrodes), or an analyte responsive surface, together with an optional conductimetric sensor or sensors. The cutaway 610 may house a ground electrode if needed as a return current path for an electrochemical sensor, and may also house an optional conductimetric sensor. A cutaway 615 may provide a fluid path between gasket holes 535 and 540 such that fluid may pass between the conduits 490 and 510. Recess 475 houses a fluid-containing package, e.g., a rupturable pouch, in the assembled cartridge 400 that may be pierced by the spike 480 because of pressure exerted upon paddle 455 upon insertion of the cartridge 400 into the reading device. Fluid from the pierced package flows into the conduit 485. The air bladder may be comprised of the recess 465, which is sealed on its upper surface by the gasket 415. The air bladder may be one embodiment of a pump means, and may be actuated by pressure applied to the paddle 460, which displaces air in the conduit 580 and thereby displaces the sample from the sample chamber 440 into the conduit 510.

In some embodiments, a metering means may optionally comprise the sample chamber 440 bounded by the capillary stop 565 and having along the chamber 440 length an air entry point (gasket hole 550) from the bladder. Air pressure exerted at the gasket hole 550 drives a metered volume of the sample past the capillary stop 565. Therefore, a metered volume of sample may be predetermined by a volume of the sample chamber 440 between the air entry point 550 and the capillary stop 565. An amount of the sample corresponding to this volume may be displaced into the conduit 510 when the paddle 460 is displaced. This arrangement may therefore provide a metering means for delivering a metered amount of an unmetered sample into the various downstream conduits of the cartridge 400. The metering may be advantageous in some embodiments if quantitation of the analyte is required. Thus, an operator may be relieved of accurately measuring the volume of the sample prior to measurement saving time, effort, and increasing the accuracy and reproducibility.

Figure 11:
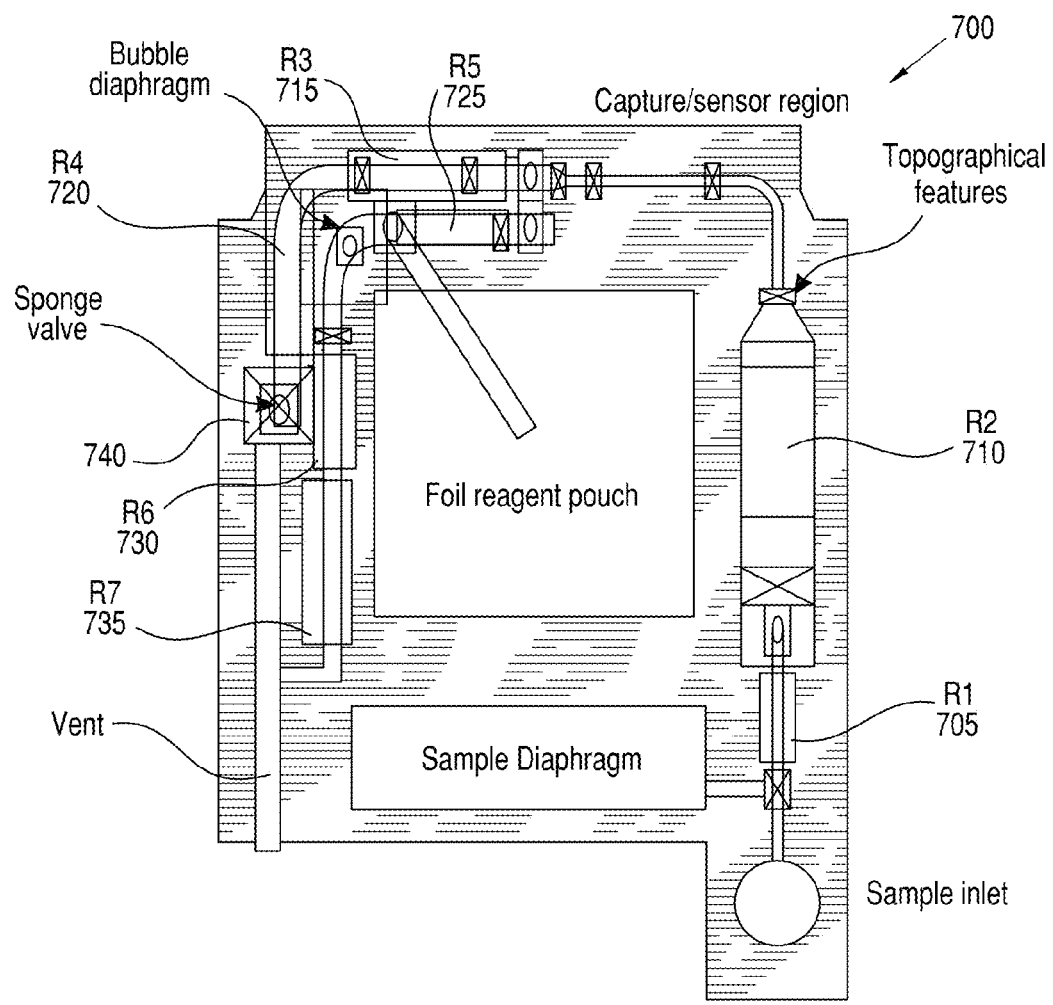
FIG. 11 shows a schematic view of the layout of a biosensor cartridge in accordance with some aspects of the invention.

As shown in FIG. 11, a schematic diagram of the features of the cartridge 700 and components therein is provided. Specifically, in preferred embodiments, the conduits and the sample chamber 705-735 may be coated with dry reagents to amend the sample or fluid as discussed herein. The sample or fluid may be passed at least once over the dry reagent to dissolve the dry reagent. Reagents that may be used to amend samples or fluid within the cartridge include enzymes, a water soluble protein, a buffer, scavengers, or combinations thereof, and/or blocking agents that prevent either specific or non-specific binding reactions among assay compounds. A surface coating that may not be soluble but helps prevent non-specific adsorption of assay components to the inner surfaces of the cartridge 700 may also be provided For example, within a segment of the sample or fluid, an amending substance may be preferentially dissolved and concentrated within a predetermined region of the segment. In one embodiment, this may be achieved through control of the position and movement of the segment within the conduits and the sample chamber 705-735. Therefore, if only a portion of a segment, such as the leading edge, is reciprocated over the amended substance, then a high local concentration of the substance can be achieved close to the leading edge. Alternatively, if a homogenous distribution of the substance is desired, for example if a known concentration of an amending substance is required for a quantitative analysis, then further reciprocation of the sample or fluid may result in mixing and an even distribution.

In preferred embodiments, a closeable valve 740 may be provided between a first conduit and the waste chamber. In one embodiment, the valve 740 may be comprised of a dried sponge material that is coated with an impermeable substance. In operation, contacting the sponge material with the sample or a fluid may result in swelling of the sponge to fill the cavity (e.g., the valve 590 cavity as shown in FIG. 10), thereby substantially blocking further flow of liquid into the waste chamber. Furthermore, the wetted valve 740 may also be configured to block the flow of air between the first conduit and the waste chamber, which permits a first pump means connected to the sample chamber to displace fluid within a second conduit, and to displace fluid from the second conduit into the first conduit in the following manner.

After the sample is exposed to the sensor array for a controlled time, the sample may be moved into a post-analytical conduit where the sample may be amended with another reagent. The sample may then be moved back to the sensor array and a second reaction period may begin. Alternately, the post-analysis conduit may serve simply to separate the sample segment from the sensor array. Within the post-analysis conduit may be a single closeable valve that connects an air vent of the sensor conduit to a diaphragm air pump. When the single closeable valve closes, the sample may be locked in the post analytical conduit and cannot be moved back to the sensor array.

In a preferred embodiment of the present invention, the sample and a fluid, e.g., a combined wash and substrate delivery fluid, may contact the sensor array at different times during an assay sequence. The sample and the fluid may also be independently amended with other reagents or compounds present initially as dry coatings within respective conduits of a test device, e.g., the cartridge. Controlled motion of the fluid by the above-described pumping means within the cartridge further permits more than one substance to be amended into each fluid whenever the sample or the fluid is moved to a new region of the conduit. In this manner, multiple amendments to each fluid may be accommodated, extending the complexity of automated assays that can be performed in the cartridge. Therefore, the utility of the present invention may be enhanced.

In an alternative embodiment, as shown in FIGS. 12A-12E, the cartridge 900 may include a housing that comprises two complimentary halves of a cartridge (e.g., the cover 901 and the base 902), which can be bonded together to abut and attach the two complimentary interior surfaces of the two halves in a closed position. In some embodiments, the cover 901 and the base 902 are injection molded, for example, by machine as disclosed in U.S. patent application Ser. No. 13/530,501, filed on Jun. 22, 2012, which is incorporated herein by reference in its entirety. Preferably, the cover 901 is injection molded where a first substantially rigid zone 920 is formed in a first injection molding step and a substantially flexible zone 922 is formed in an additional injection molding step. Preferably, the base 902 is injection molded where a second substantially rigid zone 924 is formed in a first injection molding step.

As shown in FIGS. 12A-12E, the substantially rigid zones 920 and 924 of the cover 901 and the base 902, respectively, are preferably each a single contiguous zone; however, the molding process can provide a plurality of non-contiguous substantially rigid zones. The substantially flexible zone 922 is preferably a set of several non-contiguous zones. For example, the substantially flexible zone 922 around a displaceable membrane 925 may be separate and distinct from the substantially flexible zone at a closeable sealing member 928. Alternatively, the substantially flexible zone may comprise a single contiguous zone.

In a preferred embodiment, the cartridge housing comprises a sensor recess 930 in a portion of the substantially flexible zone. An advantage is that the sensors 935, which are disposed in the sensor recess 930 preferably are made on a silicon wafer substrate, which is relatively brittle. Thus, providing a substantially flexible sensor recess 930 results in a suitable support that can protect the sensor from cracking during assembly. Note that other non-silicon based sensors may be used, e.g., those made on a plastic substrate; however, the preferred embodiment uses sensors of the type described in U.S. Pat. Nos. 5,200,051; 5,514,253; and 6,030,827, the entireties of which are incorporated herein by reference. In addition to being substantially flexible, sensor recess 930 may be best selected to form a liquid-tight and/or air-tight seal around the sensor perimeter, thereby ensuring that liquids do not leak out of the conduit that covers the sensor in the fully assembled cartridge. In an alternative embodiment, sensor recess 930 can be formed in a portion of the substantially rigid zone (as shown in FIG. 10) of either or both of the cover or the bottom of the housing. In this aspect, a liquid-tight and/or air-tight seal optionally may be formed by the double-sided adhesive sheet 415 or gasket (as shown in FIG. 9).

With regard to overall dimensions, the preferred embodiment of the molded parts shown in FIGS. 12A-12E include the cover 901 with dimensions of about 6.0 cm×3.0 cm×0.2 cm and the base 902 with dimensions of about 5.0 cm×3.0 cm×0.2 cm to provide a cartridge 900 with dimensions of about 6.0 cm×3.0 cm×0.4 cm. In terms of ranges, the cartridge 900 optionally has a length of from 1 to 50 cm, e.g., from 5 to 15 cm, a width of from 0.5 to 15 cm, e.g., from 1 to 6 cm, and a thickness of from 0.1 to 2 cm, e.g., from 0.1 to 1 cm.

Processes for Target Analyte Detection Using a Hybrid Enzyme

In preferred embodiments, the invention is a process for using a cartridge to determine the presence and/or concentration of a target analyte in a sample. The process may include introducing an unmetered fluid sample into the sample chamber 440 of the cartridge 400 through the sample entry port 445 (as shown in FIGS. 7-10). Capillary stop 565 prevents passage of the sample into conduit 510 at this stage, and conduit 440 is filled with the sample. Lid 435 is closed to prevent leakage of the sample from the cartridge. The cartridge may then be inserted into the reading device or apparatus 302, as shown in FIG. 6 and further disclosed in U.S. Pat. No. 5,821,399, which is incorporated herein by reference in its entirety. Insertion of the cartridge into the reading apparatus activates a mechanism, which punctures the fluid-containing package located at recess 475 when the package is pressed against spike 480. Fluid is thereby expelled into the conduits 485 and 490, arriving in sequence at the sensor region. The constriction 520 prevents further movement of fluid because residual hydrostatic pressure is dissipated by the flow of fluid via the conduit 585 into the waste chamber 560.

In a second step, operation of a pump means applies pressure to the air-bladder comprised of cavity 465, forcing air through the conduit 580 and into conduit 440 at a predetermined location. Capillary stop 565 delimits a metered portion of the original sample. While the sample is within sample chamber 440, it is preferably amended with a compound or compounds (e.g., enzymes, a water soluble protein, a buffer, scavengers, or a combination thereof) present initially as a dry coating or layer(s) on the inner surface of the chamber or conduits. The metered portion of the sample is then expelled through the capillary stop 565 by air pressure produced within air bladder comprised of cavity 465. The sample passes into the sensor conduit and into contact with the pair of electrodes and optionally the reference electrode located within the cutaway 605.

To promote proteolytic degradation of the hybrid enzyme immobilized on or near the electrodes, the sample containing the analyte (e.g., a protease) may optionally be passed repeatedly over the electrodes in an oscillatory motion. Preferably, an oscillation frequency of between about 0.2 and 2 Hz is used, most preferably 0.7 Hz. After a period, e.g., 10 minutes, for the proteolytic degradation of the hybrid enzyme, the sample may be ejected by further pressure applied to the air bladder comprised of cavity 465, and the sample passes to waste chamber 560. A wash step next removes any remaining protease from the sensor chamber. Fluid in the conduit 490 may be moved by a pump means, into contact with the sensors. The analysis fluid (e.g., cognate substrate) may be pulled slowly until a first air segment is detected at a conductivity sensor. Note that it may be an object of the invention that the rinsing is not sufficiently protracted or vigorous as to promote dissociation of the hybrid enzyme from the sensors.

Use of a cartridge with a closeable valve, preferably located between the sensor chamber and the waste chamber, is herein illustrated by a specific embodiment in which the concentration of thrombin is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the electrodes/sensors through pads, and performs certain diagnostic tests. Insertion of the cartridge perforates the foil pouch introducing fluid into a conduit as previously described. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the analyte determination.

Various options exist for managing any temperature effect on an assay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value Between t=1.5 and t=6.75, a metered portion of the sample, preferably between 4 and 200 uL, more preferably between 4 and 20 uL, and most preferably 7 uL, may be used to contact the electrodes/sensors as described above. The edges defining the forward and trailing edges of the sample are reciprocally moved over the sensor region at a frequency that is preferably between 0.2 to 2.0 Hz, and is most preferably 0.7 Hz. During this time, any protease in the sample that recognizes the mutated protease cleavage recognition sequence may perform cleavage of the hybrid enzyme at the cleaving sites, as previously described.

Between t=6.75 and t=10.0 the sample may be moved into the waste chamber via the closeable valve, preferably wetting the closeable valve and causing it to swell and close. The seal created by the closing of the valve permits the first pump means to be used to control motion of fluid from the sensor conduit to the post analysis conduit. After the valve closes and any remaining sample is locked in the post analysis conduit, the analyzer plunger retracts from the flexible diaphragm of the pump means creating a partial vacuum in the sensor conduit. This forces the analysis fluid (e.g., cognate substrate) through the small hole in the tape gasket and into a short transecting conduit in the base. The analysis fluid is then pulled further and the front edge of the analysis fluid is oscillated across the surface of the sensor chip in order to shear the sample near the walls of the conduit. A conductivity sensor on the sensor chip may be used to control this process. The efficiency of the process may be monitored using the amperometric sensors. The amperometric electrodes may be polarized to 250-300 mV versus the silver chloride reference-ground electrode. In this embodiment, the fluid may be composed of a carbonate or diethanolamine buffer and a cognate composition of matter such as L-glutamate. The efficiency of the wash is optimally further enhanced by introduction into the fluid of one or more segments that segment the fluid within the conduit as previously described. Following removal of wash fluid from the sensor channel leaving a thin layer of fluid over the two sensors, measurement of each sensor response is recorded and the concentration of analyte determined as described above.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A method for detecting a target analyte that exhibits protease enzyme activity, the method comprising:
    contacting a sample with a hybrid glutamate oxidase enzyme engineered to exhibit increased catalytic activity over that of a starting glutamate oxidase enzyme upon cleavage of a mutated protease cleavage recognition sequence, wherein the mutated protease cleavage recognition sequence is a recognition sequence specific for the target analyte;
    contacting a substrate with the engineered hybrid glutamate oxidase enzyme, wherein the substrate comprises a cognate composition of matter to the engineered hybrid glutamate oxidase enzyme, and the engineered hybrid glutamate oxidase enzyme is configured to catalyze conversion of the cognate composition of matter into a detectable product upon proteolytic cleavage of the mutated protease cleavage recognition sequence by the target analyte; and
    generating a detectable signal related to the detectable product;
    wherein the hybrid glutamate oxidase enzyme is SEQ ID NO: 8 or SEQ ID NO: 10.

2. The method of claim 1, wherein:
    the detectable product is hydrogen peroxide; and
    the detectable signal is generated by an electrochemical sensor or a colorimetric detection system.

3. The method of claim 1, wherein the increased catalytic activity over that of the starting glutamate oxidase enzyme is related to the protease enzyme activity of the target analyte.

4. The method of claim 1, wherein the starting glutamate oxidase enzyme is a wild-type glutamate oxidase produced by genus *Streptomyces*.

5. The method of claim 1, wherein the mutated protease cleavage recognition sequence is SEQ ID NO: 3.

* * * * *

SEQUENCE LISTING

```
<160> NUMBER OF SEQ ID NOS: 12

<210> SEQ ID NO 1
<211> LENGTH: 2147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agctggtacc atatgaacga catccgtccg ggtcaccgtc gtgaaccgtc cggtgctgaa      60
cgtgctgctg ctaaaacctg ccagcagctg gctcgtgaac tgctgctggt tggtccggaa    120
ccggctaacg aagacctgaa actgcgttac ctggacgttc tgatcgacaa cggtctggaa    180
ccgaccgctg acccgaaacg tatcctgatc gttggtgctg gtatcgctgg tctggttgct    240
ggtgacctgc tgacccgtgc tggtcacgaa gttaccatcc tggaagctaa cgctaaccgt    300
gttggtggtc gtatcaaaac cttccacgct aaaaaaggtg aaccgccgcc gttcaccgac    360
ccggctcagt acgctgaagc tggtgctatg cgtctgccgt ccttccaccc gctgaccctg    420
gctctgatcg acaaactggg tctgaaacgt cgtctgttct caacgttga catcgacccg     480 gctaccggta accagaacgc tccgctgccg ccggttgttt acaaatcctt caaagacggt    540
aaagtttgga ccaacggtgc tccgtccccg gagttccgtg ctccggacaa acgtaaccac    600
acctggatcc gtaccaaccg tacccaggtt cgtcgtgctc agtacgctaa agacccgtcc    660
gctatcaacg aaggtttcca cctgaccggt tccgcttccc gtctgccggt tgctgaaatg    720
gttcaccagg ctctggaacc ggttcgtgac tactactccg ttctgcagtc cgacggcacc    780
cgtgttaaca aaccgttcca ggaatggctg gacgttggg ctgaagttat ccgtgacttc    840
gacggttact ccatgggtcg tttcctgcgt gaatacgctg gtctgtccga cgaagctatc    900
gaagctatcg gcaccatcga aaacatgacc tcccgtctgc acctggcttt cttccactcc    960
ttcctgggtc gttccgacat cgacccgacc gctacctact gggaaatcga aggtggttcc   1020
cgtcgtctgc cggaagctct ggctaaagac ctgcgtgacc agatcgttat gggtcgtcgt   1080
atggttcgtc tggaatacta cgatccgggt cgtgacggtc accagggcac cctggctggt   1140
ccgggtggtc cggctgttgc tatccagacc gttccggaag gtgaccgta cggtgaaccg   1200 cagacctgga ccggtgacct ggctatcgtt accatcccgt tcgcttccct gcgtttcacc   1260
accgttaccc cgccgttctc ctacaaaaaa cgtcgtgctg ttatcgaaac ccactacgac   1320
caggctacca aagttctgct ggagttctcc cgtcgttggt gggagttcac cgaagctgac   1380
tggaaacgtg aactggacac catcgctccg ggtctgtacg aatactacca gcagtgggt    1440 gaagacgacg ctgaagctgc tgtttccgtt ccgcagcacc tgcgtgacct gccgaccggt   1500
ctgctgggtg ctcacccgtc cgttgacgaa aaacgtatcg gtcaggaaca ggttgaatac   1560
taccgtaact cctccctgcg tggtggtgtt cgtcggcta cccacgctgt tggtggtggt    1620
tccaccaccg acaacccgaa ccgtttcatg tactaccgt cccaccggt tccgggttcc    1680
```

```
tccggtggtg ttgttctggc tggttactcc tggtccgacg acgctgctcg ttgggactcc    1740
ttcgacgacg ctgaacgtta ctcctacgct ctgctgaacc tgcagtccgt tcacggtcgt    1800
cgtatcgaag ttttctacac cggtgctggt cagacccagt cctggctgcg tgacccgtac    1860
gcttgcggtc aagctgctgt ttacaccccg caccagatga cctccttcca cctggacgct    1920
gttcgtgctg aaggtccggt tcacttcgct ggtgaacacg tttccctgaa acacgcttgg    1980
atcgaaggtg ctgttgaaac cgctgttcgt gctgctctgg ctgttcacga atccccggct    2040
gcttgcgaat ccgctgctgc tgctcgtacc gctgaaccgg gtgaatcccg tgctgacgct    2100
accccgccgg ctccgtccca ggaagacgtt gttacctcct gaagctt                  2147
```

<210> SEQ ID NO 2
<211> LENGTH: 10
<212> TYPE: PRT
<213> ORGANISM: Streptomyces griseus

<400> SEQUENCE: 2

Ser Phe Arg Ala Pro Asp Ser Asp Asp Arg
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or Asp

<400> SEQUENCE: 3

Ile Xaa Gly Arg
1

<210> SEQ ID NO 4
<211> LENGTH: 2207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
cgggatccga gctggtacca tatgaacgac atccgtccgg gtcaccgtcg tgaaccgtcc     60
ggtgctgaac gtgctgatat cgaagcccgc gctgctaaaa cctgccagca gctggctcgt    120
gaactgctgc tggttggtcc ggaaccggct aacgaagacc tgaaactgcg ttacctggac    180
gttctgatcg acaacggtct ggaaccgacc gctgacccga acgtatcct gatcgttggt    240 gctggtatcg ctggtctggt tgctggtgac ctgctgaccc gtgctggtca cgaagttacc    300
atcctggaag ctaacgctaa ccgtgttggt ggtcgtatca aaaccttcca cgctaaaaaa    360
ggtgaaccgc cgccgttcac cgacccggct cagtacgctg aagctggtgc tatgcgtctg    420
ccgtccttcc acccgctgac cctggctctg atcgacaaac tgggtctgaa cgtcgtctg    480 ttcttcaacg ttgacatcga cccggctacc ggtaaccaga acgctccgct gccgccggtt    540
gtttacaaat ccttcaaaga cggtaaagtt tggaccaacg tgctccgtc cccggagttc    600 cgtgctccgg acaaacgtaa ccacacctgg atccgtacca accgtaccca ggttcgtcgt    660
gctcagtacg ctaaagaccc gtccgctatc aacgaaggtt ccacctgac cggttccgct    720
```

```
tcccgtctgc cggttgctga aatggttcac caggctctgg aaccggttcg tgactactac    780
tccgttctgc agtccgacgg cacccgtgtt aacaaaccgt tccaggaatg gctggacggt    840
tgggctgaag ttatccgtga cttcgacggt tactccatgg gtcgtttcct gcgtgaatac    900
gctggtctgt ccgacgaagc tatcgaagct atcggcacca tcgaaaacat gacctcccgt    960
ctgcacctgg ctttcttcca ctccttcctg ggtcgttccg acatcgaccc gaccgctacc   1020
tactgggaaa tcgaaggtgg ttcccgtcgt ctgccggaag ctctggctaa agacctgcgt   1080
gaccagatcg ttatgggtcg tcgtatggtt cgtctggaat actacgatcc gggtcgtgac   1140
ggtcaccagg gcaccctggc tattgacgct cgtgtcgacg tccgggtgg tccggctgtt   1200 gctatccaga ccgttccgga aggtgacccg tacggtgaac cgcagacctg gaccggtgac   1260
ctggctatcg ttaccatccc gttcgcttcc ctgcgtttca ccaccgttac cccgccgttc   1320
tcctacaaaa aacgtcgtgc tgttatcgaa acccactacg accaggctac caaagttctg   1380
ctggagttct cccgtcgttg gtgggagttc accgaagctg actggaaacg tgaactggac   1440
accatcgctc cgggtctgta cgaatactac cagcagtggg gtgaagacga cgctgaagct   1500
gctgtttccg ttccgcagca cctgcgtgac ctgccgaccg tctgctgggt gctcacccg    1560 tccgttgacg aaaaacgtat cggtcaggaa caggttgaat actaccgtaa ctcctccctg   1620
cgtatcgagg cccgtgaatt cggtggtgtt cgtccggcta cccacgctgt tggtggtggt   1680
tccaccaccg acaacccgaa ccgtttcatg tactacccgt cccaccccgt tccgggttcc   1740
tccggtggtg ttgttctggc tggttactcc tggtccgacg acgctgctcg ttgggactcc   1800
ttcgacgacg ctgaacgtta ctcctacgct ctgctgaacc tgcagtccgt tcacggtcgt   1860
cgtatcgaag ttttctacac cggtgctggt cagacccagt cctggctgcg tgacccgtac   1920
gcttgcggtg aagctgctgt ttacacccg caccagatga cctccttcca cctggacgct   1980
gttcgtgctg aaggtccggt tcacttcgct ggtgaacacg tttccctgaa acacgcttgg   2040
atcgaaggtg ctgttgaaac cgctgttcgt gctgctctgg ctgttcacga atcccggct    2100 gcttgcgaat ccgctgctgc tgctcgtacc gctgaaccgg gtgaatcccg tgctgacgct   2160
accccgccgg ctccgtccca ggaagacgtt gttacctcct gaagctt              2207
```

<210> SEQ ID NO 5  
<211> LENGTH: 2127  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 5

```
catatgaatt cgatgaccac cgataccgcg cgccgccata ccggcgcgga acgcgcgaac     60
gaaatgacct atgaacagct ggcgcgcgaa ctgctgctgg tgggcccggc gccgaccaac    120
gaagatctga aactgcgcta tctggatgtg ctgattgata acggcctgaa cccgccgggc    180
ccgccgaaaa cgcattctga tgtgggcgcg ggcattgcgg gcctggtggc gggcgatctg    240
ctgacccgcg cgggccatga tgtgaccatt ctggaagcga acgcgaaccg cgtgggcggc    300
cgcattaaaa cctttcatgc gaaaaaggc gaaccgagcc cgtttgcgga tccggcgcag    360
tatgcggaag cgggcgcgat gcgcctgccg agctttcatc cgctgaccct ggcgctgatt    420
gataaactgg gcctgaaacg ccgcctgttt ttaacgtgg atattgatcc gcagaccggc    480
aaccaggatg cgccggtgcc gccggtgttt tataaaagct ttaagatgg caaaacctgg    540
```

```
accaacggcg cgccgagccc ggaatttaaa gaaccggata aacgcaacca tacctggatt    600
cgcaccaacc gcgaacaggt gcgccgcgcg cagtatgcga ccgatccgag cagcattaac    660
gaaggctttc atctgaccgg ctgcgaaacc cgcctgaccg tgagcgatat ggtgaaccag    720
gcgctggaac cggtgcgcga ttattatagc gtgaaacagg atgatggcac ccgcgtgaac    780
aaaccgttta agaatggct ggcgggctgg gcggatgtgg tgcgcgattt tgatggctat    840
agcatgggcc gctttctgcg cgaatatgcg gaatttagcg atgaagcggt ggaagcgatt    900
ggcaccattg aaaacatgac cagccgcctg catctggcgt ttttcatag ctttctgggc     960 cgcagcgata ttgatccgcg cgcgacctat tgggaaattg aaggcggcag ccgcatgctg    1020
ccggaaaccc tggcgaaaga tctgcgcgat cagattgtga tgggccagcg catggtgcgc    1080
ctggaatatt atgatccggg ccgcgatggc catcatggcg aactgaccgg ccgggcggc    1140 ccggcggtgg cgattcagac cgtgccggaa ggcgaaccgt atgcggcgac ccagacctgg    1200
accggcgatc tggcgattgt gaccattccg tttagcagcc tgcgctttgt gaaagtgacc    1260
ccgccgttta gctataaaaa acgccgcgcg gtgattgaaa cccattatga tcaggcgacc    1320
aaagtgctgc tggaatttag ccgccgctgg tgggaattta ccgaagcgga ttggaaacgc    1380
gaactggatg cgattgcgcc gggcctgtat gattattatc agcagtgggg cgaagatgat    1440
gcggaagcgg cgctggcgct gccgcagagc gtgcgcaacc tgccgaccgg cctgctgggc    1500
gcgcatccga gcgtggatga aagccgcatt ggcgaagaac aggtggaata ttatcgcaac    1560
agcgaactgc gcggcggcgt gcgcccggcg accaacgcgt atggcggcgg cagcaccacc    1620
gataacccga accgctttat gtattatccg agccatccgg tgccgggcac ccagggcggc    1680
gtggtgctgg cggcgtatag ctggagcgat gatgcggcgc gctgggatag ctttgatgat    1740
gcggaacgct atggctatgc gctggaaaac ctgcagagcg tgcatggccg ccgcattgaa    1800
gtgttttata ccggcgcggg ccagacccag agctggctgc gcgatccgta tgcgtgcggc    1860
gaagcggcgg tgtatacccc gcatcagatg accgcgtttc atctggatgt ggtgcgcccg    1920
gaaggcccgg tgtattttgc gggcgaacat gtgagcctga acatgcgtg gattgaaggc     1980 gcggtggaaa ccgcggtgcg cgcggcgatt gcggtgaacg aagcgccggt gggcgatacc    2040
ggcgtgaccg cggcggcggg ccgccgcggc gcggcggcgg cgaccgaacc gatgcgcgaa    2100
gaagcgctga ccagcctcga gatatct                                       2127
```

<210> SEQ ID NO 6
<211> LENGTH: 2127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
catatgaatt cgatgaccac cgataccgcg cgccgccata ccattgaagg ccgcgcgaac     60
gaaatgacct atgaacagct ggcgcgcgaa ctgctgctgg tgggcccggc gccgaccaac    120
gaagatctga actgcgcta tctggatgtg ctgattgata acggcctgaa cccgccgggc    180
ccgccgaaac gcattctgat tgtgggcgcg ggcattgcgg gcctggtggc gggcgatctg    240
ctgacccgcg cgggccatga tgtgaccatt ctggaagcga cgcgaaccg cgtgggcggc    300 cgcattaaaa cctttcatgc gaaaaaaggc gaaccgagcc gtttgcgga tccggcgcag    360 tatgcggaag cgggcgcgat gcgcctgccg agctttcatc cgctgaccct ggcgctgatt    420
```

```
gataaactgg gcctgaaacg ccgcctgttt tttaacgtgg atattgatcc gcagaccggc      480
aaccaggatg cgccggtgcc gccggtgttt tataaaagct ttaaagatgg caaaacctgg      540
accaacggcg cgccgagccc ggaatttaaa gaaccggata acgcaacca tacctggatt      600 cgcaccaacc gcgaacaggt gcgccgcgcg cagtatgcga ccgatccgag cagcattaac      660
gaaggctttc atctgaccgg ctgcgaaacc cgcctgaccg tgagcgatat ggtgaaccag      720
gcgctggaac cggtgcgcga ttattatagc gtgaaacagg atgatggcac cgcgtgaac       780 aaaccgttta agaatggct ggcgggctgg gcggatgtgg tgcgcgattt tgatggctat       840
agcatgggcc gctttctgcg cgaatatgcg gaatttagcg atgaagcggt ggaagcgatt      900
ggcaccattg aaaacatgac cagccgcctg catctggcgt ttttcatag ctttctgggc       960 cgcagcgata ttgatccgcg cgcgacctat tgggaaattg aaggcggcag ccgcatgctg     1020
ccggaaaccc tggcgaaaga tctgcgcgat cagattgtga tgggccagcg catggtgcgc     1080
ctggaatatt atgatccggg ccgcgatggc catcatggcg aactgaccgg ccgggcggc      1140 ccggcggtgg cgattcagac cgtgccggaa ggcgaaccgt atattgaagg ccgcacctgg     1200
accggcgatc tggcgattgt gaccattccg tttagcagcc tgcgctttgt gaaagtgacc     1260
ccgccgttta gctataaaaa acgccgcgcg gtgattgaaa cccattatga tcaggcgacc     1320
aaagtgctgc tggaatttag ccgccgctgg tgggaattta ccgaagcgga ttggaaacgc     1380
gaactggatg cgattgcgcc gggcctgtat gattattatc agcagtgggg cgaagatgat     1440
gcggaagcgg cgctggcgct gccgcagagc gtgcgcaacc tgccgaccgg cctgctgggc     1500
gcgcatccga gcgtggatga agccgcatt ggcgaagaac aggtggaata ttatcgcaac      1560
agcgaaattg aaggccgcgt gcgcccggcg accaacgcgt atggcggcgg cagcaccacc     1620
gataacccga accgctttat gtattatccg agccatccgg tgccgggcac ccagggcggc     1680
gtggtgctgg cggcgtatag ctggagcgat gatgcggcgc gctgggatag ctttgatgat     1740
gcggaacgct atgctatgc gctggaaaac ctgcagagcg tgcatggccg ccgcattgaa      1800
gtgttttata ccggcgcggg ccagacccag agctggctgc gcgatccgta tgcgtgcggc     1860
gaagcggcgg tgtataccc cgcatcagatg accgcgtttc atctggatgt ggtgcgcccg     1920
gaaggcccgg tgtattttgc gggcgaacat gtgagcctga acatgcgtg gattgaaggc      1980 gcggtggaaa ccgcggtgcg cgcggcgatt gcggtgaacg aagcgccggt gggcgatacc     2040
ggcgtgaccg cggcggcggg ccgccgcggc gcggcggcgg cgaccgaacc gatgcgcgaa     2100
gaagcgctga ccagcctcga gatatct                                         2127
```

<210> SEQ ID NO 7
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Trp Tyr His Met Asn Asp Ile Arg Pro Gly His Arg Arg Glu Pro
1               5                   10                  15

Ser Gly Ala Glu Arg Ala Ala Ala Lys Thr Cys Gln Gln Leu Ala Arg
            20                  25                  30

Glu Leu Leu Leu Val Gly Pro Glu Pro Ala Asn Glu Asp Leu Lys Leu
        35                  40                  45

```
Arg Tyr Leu Asp Val Leu Ile Asp Asn Gly Leu Glu Pro Thr Ala Asp
             50                  55                  60

Pro Lys Arg Ile Leu Ile Val Gly Ala Gly Ile Ala Gly Leu Val Ala
 65                  70                  75                  80

Gly Asp Leu Leu Thr Arg Ala Gly His Glu Val Thr Ile Leu Glu Ala
                 85                  90                  95

Asn Ala Asn Arg Val Gly Gly Arg Ile Lys Thr Phe His Ala Lys Lys
                100                 105                 110

Gly Glu Pro Pro Pro Phe Thr Asp Pro Ala Gln Tyr Ala Glu Ala Gly
            115                 120                 125

Ala Met Arg Leu Pro Ser Phe His Pro Leu Thr Leu Ala Leu Ile Asp
130                 135                 140

Lys Leu Gly Leu Lys Arg Arg Leu Phe Phe Asn Val Asp Ile Asp Pro
145                 150                 155                 160

Ala Thr Gly Asn Gln Asn Ala Pro Leu Pro Pro Val Val Tyr Lys Ser
                165                 170                 175

Phe Lys Asp Gly Lys Val Trp Thr Asn Gly Ala Pro Ser Pro Glu Phe
            180                 185                 190

Arg Ala Pro Asp Lys Arg Asn His Thr Trp Ile Arg Thr Asn Arg Thr
                195                 200                 205

Gln Val Arg Arg Ala Gln Tyr Ala Lys Asp Pro Ser Ala Ile Asn Glu
    210                 215                 220

Gly Phe His Leu Thr Gly Ser Ala Ser Arg Leu Pro Val Ala Glu Met
225                 230                 235                 240

Val His Gln Ala Leu Glu Pro Val Arg Asp Tyr Tyr Ser Val Leu Gln
                245                 250                 255

Ser Asp Gly Thr Arg Val Asn Lys Pro Phe Gln Glu Trp Leu Asp Gly
            260                 265                 270

Trp Ala Glu Val Ile Arg Asp Phe Asp Gly Tyr Ser Met Gly Arg Phe
        275                 280                 285

Leu Arg Glu Tyr Ala Gly Leu Ser Asp Glu Ala Ile Glu Ala Ile Gly
    290                 295                 300

Thr Ile Glu Asn Met Thr Ser Arg Leu His Leu Ala Phe Phe His Ser
305                 310                 315                 320

Phe Leu Gly Arg Ser Asp Ile Asp Pro Thr Ala Thr Tyr Trp Glu Ile
                325                 330                 335

Glu Gly Gly Ser Arg Arg Leu Pro Glu Ala Leu Ala Lys Asp Leu Arg
            340                 345                 350

Asp Gln Ile Val Met Gly Arg Arg Met Val Arg Leu Glu Tyr Tyr Asp
        355                 360                 365

Pro Gly Arg Asp Gly His Gln Gly Thr Leu Ala Gly Pro Gly Gly Pro
    370                 375                 380

Ala Val Ala Ile Gln Thr Val Pro Glu Gly Asp Pro Tyr Gly Glu Pro
385                 390                 395                 400

Gln Thr Trp Thr Gly Asp Leu Ala Ile Val Thr Ile Pro Phe Ala Ser
                405                 410                 415

Leu Arg Phe Thr Thr Val Thr Pro Pro Phe Ser Tyr Lys Lys Arg Arg
            420                 425                 430

Ala Val Ile Glu Thr His Tyr Asp Gln Ala Thr Lys Val Leu Leu Glu
        435                 440                 445

Phe Ser Arg Arg Trp Trp Glu Phe Thr Glu Ala Asp Trp Lys Arg Glu
    450                 455                 460

Leu Asp Thr Ile Ala Pro Gly Leu Tyr Glu Tyr Tyr Gln Gln Trp Gly
```

```
            465                 470                 475                 480
    Glu Asp Asp Ala Glu Ala Ala Val Ser Val Pro Gln His Leu Arg Asp
                    485                 490                 495
    Leu Pro Thr Gly Leu Leu Gly Ala His Pro Ser Val Asp Glu Lys Arg
                500                 505                 510
    Ile Gly Gln Glu Gln Val Glu Tyr Tyr Arg Asn Ser Ser Leu Arg Gly
                515                 520                 525
    Gly Val Arg Pro Ala Thr His Ala Val Gly Gly Ser Thr Thr Asp
            530                 535                 540
    Asn Pro Asn Arg Phe Met Tyr Tyr Pro Ser His Pro Val Pro Gly Ser
    545                 550                 555                 560
    Ser Gly Gly Val Val Leu Ala Gly Tyr Ser Trp Ser Asp Asp Ala Ala
                    565                 570                 575
    Arg Trp Asp Ser Phe Asp Ala Glu Arg Tyr Ser Tyr Ala Leu Leu
                580                 585                 590
    Asn Leu Gln Ser Val His Gly Arg Arg Ile Glu Val Phe Tyr Thr Gly
                595                 600                 605
    Ala Gly Gln Thr Gln Ser Trp Leu Arg Asp Pro Tyr Ala Cys Gly Glu
            610                 615                 620
    Ala Ala Val Tyr Thr Pro His Gln Met Thr Ser Phe His Leu Asp Ala
    625                 630                 635                 640
    Val Arg Ala Glu Gly Pro Val His Phe Ala Gly Glu His Val Ser Leu
                    645                 650                 655
    Lys His Ala Trp Ile Glu Gly Ala Val Glu Thr Ala Val Arg Ala Ala
                660                 665                 670
    Leu Ala Val His Glu Ser Pro Ala Ala Cys Glu Ser Ala Ala Ala Ala
                675                 680                 685
    Arg Thr Ala Glu Pro Gly Glu Ser Arg Ala Asp Ala Thr Pro Pro Ala
            690                 695                 700
    Pro Ser Gln Glu Asp Val Val Thr Ser
    705                 710

<210> SEQ ID NO 8
<211> LENGTH: 733
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Asp Pro Ser Trp Tyr His Met Asn Asp Ile Arg Pro Gly His Arg
1               5                   10                  15
Arg Glu Pro Ser Gly Ala Glu Arg Ala Asp Ile Glu Ala Arg Ala Ala
                20                  25                  30
Lys Thr Cys Gln Gln Leu Ala Arg Glu Leu Leu Val Gly Pro Glu
            35                  40                  45
Pro Ala Asn Glu Asp Leu Lys Leu Arg Tyr Leu Asp Val Leu Ile Asp
        50                  55                  60
Asn Gly Leu Glu Pro Thr Ala Asp Pro Lys Arg Ile Leu Ile Val Gly
65                  70                  75                  80
Ala Gly Ile Ala Gly Leu Val Ala Gly Asp Leu Leu Thr Arg Ala Gly
                85                  90                  95
His Glu Val Thr Ile Leu Glu Ala Asn Ala Asn Arg Val Gly Gly Arg
            100                 105                 110
```

```
Ile Lys Thr Phe His Ala Lys Lys Gly Glu Pro Pro Phe Thr Asp
            115                 120                 125
Pro Ala Gln Tyr Ala Glu Ala Gly Ala Met Arg Leu Pro Ser Phe His
    130                 135                 140
Pro Leu Thr Leu Ala Leu Ile Asp Lys Leu Gly Leu Lys Arg Arg Leu
145                 150                 155                 160
Phe Phe Asn Val Asp Ile Asp Pro Ala Thr Gly Asn Gln Asn Ala Pro
                165                 170                 175
Leu Pro Pro Val Val Tyr Lys Ser Phe Lys Asp Gly Lys Val Trp Thr
            180                 185                 190
Asn Gly Ala Pro Ser Pro Glu Phe Arg Ala Pro Asp Lys Arg Asn His
        195                 200                 205
Thr Trp Ile Arg Thr Asn Arg Thr Gln Val Arg Arg Ala Gln Tyr Ala
    210                 215                 220
Lys Asp Pro Ser Ala Ile Asn Glu Gly Phe His Leu Thr Gly Ser Ala
225                 230                 235                 240
Ser Arg Leu Pro Val Ala Glu Met Val His Gln Ala Leu Glu Pro Val
                245                 250                 255
Arg Asp Tyr Tyr Ser Val Leu Gln Ser Asp Gly Thr Arg Val Asn Lys
            260                 265                 270
Pro Phe Gln Glu Trp Leu Asp Gly Trp Ala Glu Val Ile Arg Asp Phe
        275                 280                 285
Asp Gly Tyr Ser Met Gly Arg Phe Leu Arg Glu Tyr Ala Gly Leu Ser
    290                 295                 300
Asp Glu Ala Ile Glu Ala Ile Gly Thr Ile Glu Asn Met Thr Ser Arg
305                 310                 315                 320
Leu His Leu Ala Phe Phe His Ser Phe Leu Gly Arg Ser Asp Ile Asp
                325                 330                 335
Pro Thr Ala Thr Tyr Trp Glu Ile Glu Gly Gly Ser Arg Arg Leu Pro
            340                 345                 350
Glu Ala Leu Ala Lys Asp Leu Arg Asp Gln Ile Val Met Gly Arg Arg
        355                 360                 365
Met Val Arg Leu Glu Tyr Tyr Asp Pro Gly Arg Asp Gly His Gln Gly
    370                 375                 380
Thr Leu Ala Ile Asp Ala Arg Val Asp Gly Pro Gly Gly Pro Ala Val
385                 390                 395                 400
Ala Ile Gln Thr Val Pro Glu Gly Asp Pro Tyr Gly Glu Pro Gln Thr
                405                 410                 415
Trp Thr Gly Asp Leu Ala Ile Val Thr Ile Pro Phe Ala Ser Leu Arg
            420                 425                 430
Phe Thr Thr Val Thr Pro Pro Phe Ser Tyr Lys Lys Arg Arg Ala Val
        435                 440                 445
Ile Glu Thr His Tyr Asp Gln Ala Thr Lys Val Leu Leu Glu Phe Ser
    450                 455                 460
Arg Arg Trp Trp Glu Phe Thr Glu Ala Asp Trp Lys Arg Glu Leu Asp
465                 470                 475                 480
Thr Ile Ala Pro Gly Leu Tyr Glu Tyr Gln Gln Trp Gly Glu Asp
                485                 490                 495
Asp Ala Glu Ala Ala Val Ser Val Pro Gln His Leu Arg Asp Leu Pro
            500                 505                 510
Thr Gly Leu Leu Gly Ala His Pro Ser Val Asp Glu Lys Arg Ile Gly
        515                 520                 525
Gln Glu Gln Val Glu Tyr Tyr Arg Asn Ser Ser Leu Arg Ile Glu Ala
```

```
                530             535             540
Arg Glu Phe Gly Gly Val Arg Pro Ala Thr His Ala Val Gly Gly
545             550             555             560

Ser Thr Thr Asp Asn Pro Asn Arg Phe Met Tyr Tyr Pro Ser His Pro
                565             570             575

Val Pro Gly Ser Ser Gly Gly Val Val Leu Ala Gly Tyr Ser Trp Ser
            580             585             590

Asp Asp Ala Ala Arg Trp Asp Ser Phe Asp Asp Ala Glu Arg Tyr Ser
            595             600             605

Tyr Ala Leu Leu Asn Leu Gln Ser Val His Gly Arg Arg Ile Glu Val
        610             615             620

Phe Tyr Thr Gly Ala Gly Gln Thr Gln Ser Trp Leu Arg Asp Pro Tyr
625             630             635             640

Ala Cys Gly Glu Ala Ala Val Tyr Thr Pro His Gln Met Thr Ser Phe
            645             650             655

His Leu Asp Ala Val Arg Ala Glu Gly Pro Val His Phe Ala Gly Glu
            660             665             670

His Val Ser Leu Lys His Ala Trp Ile Glu Gly Ala Val Glu Thr Ala
        675             680             685

Val Arg Ala Ala Leu Ala Val His Glu Ser Pro Ala Ala Cys Glu Ser
690             695             700

Ala Ala Ala Ala Arg Thr Ala Glu Pro Gly Glu Ser Arg Ala Asp Ala
705             710             715             720

Thr Pro Pro Ala Pro Ser Gln Glu Asp Val Val Thr Ser
                725             730
```

<210> SEQ ID NO 9
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
His Met Asn Ser Met Thr Thr Asp Thr Ala Arg Arg His Thr Gly Ala
1               5                   10                  15

Glu Arg Ala Asn Glu Met Thr Tyr Glu Gln Leu Ala Arg Glu Leu Leu
            20                  25                  30

Leu Val Gly Pro Ala Pro Thr Asn Glu Asp Leu Lys Leu Arg Tyr Leu
        35                  40                  45

Asp Val Leu Ile Asp Asn Gly Leu Asn Pro Pro Gly Pro Pro Lys Arg
    50                  55                  60

Ile Leu Ile Val Gly Ala Gly Ile Ala Gly Leu Val Ala Gly Asp Leu
65                  70                  75                  80

Leu Thr Arg Ala Gly His Asp Val Thr Ile Leu Glu Ala Asn Ala Asn
                85                  90                  95

Arg Val Gly Gly Arg Ile Lys Thr Phe His Ala Lys Lys Gly Glu Pro
            100                 105                 110

Ser Pro Phe Ala Asp Pro Ala Gln Tyr Ala Glu Ala Gly Ala Met Arg
        115                 120                 125

Leu Pro Ser Phe His Pro Leu Thr Leu Ala Leu Ile Asp Lys Leu Gly
    130                 135                 140

Leu Lys Arg Arg Leu Phe Phe Asn Val Asp Ile Asp Pro Gln Thr Gly
145                 150                 155                 160
```

-continued

```
Asn Gln Asp Ala Pro Val Pro Val Phe Tyr Lys Ser Phe Lys Asp
                165                 170                 175
Gly Lys Thr Trp Thr Asn Gly Ala Pro Ser Pro Glu Phe Lys Glu Pro
        180                 185                 190
Asp Lys Arg Asn His Thr Trp Ile Arg Thr Asn Arg Glu Gln Val Arg
        195                 200                 205
Arg Ala Gln Tyr Ala Thr Asp Pro Ser Ser Ile Asn Glu Gly Phe His
210                 215                 220
Leu Thr Gly Cys Glu Thr Arg Leu Thr Val Ser Asp Met Val Asn Gln
225                 230                 235                 240
Ala Leu Glu Pro Val Arg Asp Tyr Tyr Ser Val Lys Gln Asp Asp Gly
                245                 250                 255
Thr Arg Val Asn Lys Pro Phe Lys Glu Trp Leu Ala Gly Trp Ala Asp
                260                 265                 270
Val Val Arg Asp Phe Asp Gly Tyr Ser Met Gly Arg Phe Leu Arg Glu
                275                 280                 285
Tyr Ala Glu Phe Ser Asp Glu Ala Val Glu Ala Ile Gly Thr Ile Glu
                290                 295                 300
Asn Met Thr Ser Arg Leu His Leu Ala Phe Phe His Ser Phe Leu Gly
305                 310                 315                 320
Arg Ser Asp Ile Asp Pro Arg Ala Thr Tyr Trp Glu Ile Glu Gly Gly
                325                 330                 335
Ser Arg Met Leu Pro Glu Thr Leu Ala Lys Asp Leu Arg Asp Gln Ile
                340                 345                 350
Val Met Gly Gln Arg Met Val Arg Leu Glu Tyr Tyr Asp Pro Gly Arg
                355                 360                 365
Asp Gly His His Gly Glu Leu Thr Gly Pro Gly Pro Ala Val Ala
        370                 375                 380
Ile Gln Thr Val Pro Glu Gly Glu Pro Tyr Ala Ala Thr Gln Thr Trp
385                 390                 395                 400
Thr Gly Asp Leu Ala Ile Val Thr Ile Pro Phe Ser Ser Leu Arg Phe
                405                 410                 415
Val Lys Val Thr Pro Pro Phe Ser Tyr Lys Lys Arg Arg Ala Val Ile
                420                 425                 430
Glu Thr His Tyr Asp Gln Ala Thr Lys Val Leu Leu Glu Phe Ser Arg
        435                 440                 445
Arg Trp Trp Glu Phe Thr Glu Ala Asp Trp Lys Arg Glu Leu Asp Ala
        450                 455                 460
Ile Ala Pro Gly Leu Tyr Asp Tyr Tyr Gln Gln Trp Gly Glu Asp Asp
465                 470                 475                 480
Ala Glu Ala Ala Leu Ala Leu Pro Gln Ser Val Arg Asn Leu Pro Thr
                485                 490                 495
Gly Leu Leu Gly Ala His Pro Ser Val Asp Glu Ser Arg Ile Gly Glu
                500                 505                 510
Glu Gln Val Glu Tyr Tyr Arg Asn Ser Glu Leu Arg Gly Gly Val Arg
        515                 520                 525
Pro Ala Thr Asn Ala Tyr Gly Gly Ser Thr Thr Asp Asn Pro Asn
530                 535                 540
Arg Phe Met Tyr Tyr Pro Ser His Pro Val Pro Gly Thr Gln Gly Gly
545                 550                 555                 560
Val Val Leu Ala Ala Tyr Ser Trp Ser Asp Asp Ala Ala Arg Trp Asp
                565                 570                 575
Ser Phe Asp Asp Ala Glu Arg Tyr Gly Tyr Ala Leu Glu Asn Leu Gln
```

```
                    580                 585                 590
Ser Val His Gly Arg Arg Ile Glu Val Phe Tyr Thr Gly Ala Gly Gln
                595                 600                 605

Thr Gln Ser Trp Leu Arg Asp Pro Tyr Ala Cys Gly Glu Ala Ala Val
    610                 615                 620

Tyr Thr Pro His Gln Met Thr Ala Phe His Leu Asp Val Val Arg Pro
625                 630                 635                 640

Glu Gly Pro Val Tyr Phe Ala Gly Glu His Val Ser Leu Lys His Ala
                645                 650                 655

Trp Ile Glu Gly Ala Val Glu Thr Ala Val Arg Ala Ala Ile Ala Val
            660                 665                 670

Asn Glu Ala Pro Val Gly Asp Thr Gly Val Thr Ala Ala Gly Arg
        675                 680                 685

Arg Gly Ala Ala Ala Thr Glu Pro Met Arg Glu Ala Leu Thr
    690                 695                 700

Ser Leu Glu Ile Ser
705

<210> SEQ ID NO 10
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Met Asn Ser Met Thr Thr Asp Thr Ala Arg Arg His Thr Ile Glu
1               5                   10                  15

Gly Arg Ala Asn Glu Met Thr Tyr Glu Gln Leu Ala Arg Glu Leu Leu
            20                  25                  30

Leu Val Gly Pro Ala Pro Thr Asn Glu Asp Leu Lys Leu Arg Tyr Leu
        35                  40                  45

Asp Val Leu Ile Asp Asn Gly Leu Asn Pro Pro Gly Pro Pro Lys Arg
    50                  55                  60

Ile Leu Ile Val Gly Ala Gly Ile Ala Gly Leu Val Ala Gly Asp Leu
65                  70                  75                  80

Leu Thr Arg Ala Gly His Asp Val Thr Ile Leu Glu Ala Asn Ala Asn
                85                  90                  95

Arg Val Gly Gly Arg Ile Lys Thr Phe His Ala Lys Lys Gly Glu Pro
            100                 105                 110

Ser Pro Phe Ala Asp Pro Ala Gln Tyr Ala Glu Ala Gly Ala Met Arg
        115                 120                 125

Leu Pro Ser Phe His Pro Leu Thr Leu Ala Leu Ile Asp Lys Leu Gly
    130                 135                 140

Leu Lys Arg Arg Leu Phe Phe Asn Val Asp Ile Asp Pro Gln Thr Gly
145                 150                 155                 160

Asn Gln Asp Ala Pro Val Pro Val Phe Tyr Lys Ser Phe Lys Asp
                165                 170                 175

Gly Lys Thr Trp Thr Asn Gly Ala Pro Ser Pro Glu Phe Lys Glu Pro
            180                 185                 190

Asp Lys Arg Asn His Thr Trp Ile Arg Thr Asn Arg Glu Gln Val Arg
        195                 200                 205

Arg Ala Gln Tyr Ala Thr Asp Pro Ser Ser Ile Asn Glu Gly Phe His
    210                 215                 220
```

```
Leu Thr Gly Cys Glu Thr Arg Leu Thr Val Ser Asp Met Val Asn Gln
225                 230                 235                 240

Ala Leu Glu Pro Val Arg Asp Tyr Tyr Ser Val Lys Gln Asp Asp Gly
            245                 250                 255

Thr Arg Val Asn Lys Pro Phe Lys Glu Trp Leu Ala Gly Trp Ala Asp
                260                 265                 270

Val Val Arg Asp Phe Asp Gly Tyr Ser Met Gly Arg Phe Leu Arg Glu
            275                 280                 285

Tyr Ala Glu Phe Ser Asp Glu Ala Val Glu Ala Ile Gly Thr Ile Glu
            290                 295                 300

Asn Met Thr Ser Arg Leu His Leu Ala Phe Phe His Ser Phe Leu Gly
305                 310                 315                 320

Arg Ser Asp Ile Asp Pro Arg Ala Thr Tyr Trp Glu Ile Glu Gly Gly
                325                 330                 335

Ser Arg Met Leu Pro Glu Thr Leu Ala Lys Asp Leu Arg Asp Gln Ile
            340                 345                 350

Val Met Gly Gln Arg Met Val Arg Leu Glu Tyr Tyr Asp Pro Gly Arg
            355                 360                 365

Asp Gly His His Gly Glu Leu Thr Gly Pro Gly Pro Ala Val Ala
370                 375                 380

Ile Gln Thr Val Pro Glu Gly Glu Pro Tyr Ile Glu Gly Arg Thr Trp
385                 390                 395                 400

Thr Gly Asp Leu Ala Ile Val Thr Ile Pro Phe Ser Ser Leu Arg Phe
                405                 410                 415

Val Lys Val Thr Pro Pro Phe Ser Tyr Lys Lys Arg Arg Ala Val Ile
            420                 425                 430

Glu Thr His Tyr Asp Gln Ala Thr Lys Val Leu Leu Glu Phe Ser Arg
            435                 440                 445

Arg Trp Trp Glu Phe Thr Glu Ala Asp Trp Lys Arg Glu Leu Asp Ala
            450                 455                 460

Ile Ala Pro Gly Leu Tyr Asp Tyr Tyr Gln Gln Trp Gly Glu Asp Asp
465                 470                 475                 480

Ala Glu Ala Ala Leu Ala Leu Pro Gln Ser Val Arg Asn Leu Pro Thr
            485                 490                 495

Gly Leu Leu Gly Ala His Pro Ser Val Asp Glu Ser Arg Ile Gly Glu
            500                 505                 510

Glu Gln Val Glu Tyr Tyr Arg Asn Ser Glu Ile Glu Gly Arg Val Arg
            515                 520                 525

Pro Ala Thr Asn Ala Tyr Gly Gly Ser Thr Thr Asp Asn Pro Asn
530                 535                 540

Arg Phe Met Tyr Tyr Pro Ser His Pro Val Pro Gly Thr Gln Gly Gly
545                 550                 555                 560

Val Val Leu Ala Ala Tyr Ser Trp Ser Asp Asp Ala Ala Arg Trp Asp
            565                 570                 575

Ser Phe Asp Asp Ala Glu Arg Tyr Gly Tyr Ala Leu Glu Asn Leu Gln
            580                 585                 590

Ser Val His Gly Arg Arg Ile Glu Val Phe Tyr Thr Gly Ala Gly Gln
            595                 600                 605

Thr Gln Ser Trp Leu Arg Asp Pro Tyr Ala Cys Gly Glu Ala Ala Val
            610                 615                 620

Tyr Thr Pro His Gln Met Thr Ala Phe His Leu Asp Val Val Arg Pro
625                 630                 635                 640

Glu Gly Pro Val Tyr Phe Ala Gly Glu His Val Ser Leu Lys His Ala
```

```
                    645                 650                 655
Trp Ile Glu Gly Ala Val Glu Thr Ala Val Arg Ala Ala Ile Ala Val
                660                 665                 670

Asn Glu Ala Pro Val Gly Asp Thr Gly Val Thr Ala Ala Ala Gly Arg
            675                 680                 685

Arg Gly Ala Ala Ala Ala Thr Glu Pro Met Arg Glu Glu Ala Leu Thr
        690                 695                 700

Ser Leu Glu Ile Ser
705

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Thr Glu Ala Asp Trp Lys Arg Glu Leu Asp Thr Ile
1               5                   10
```